United States Patent
Boileau et al.

(10) Patent No.: US 9,821,015 B2
(45) Date of Patent: *Nov. 21, 2017

(54) METHODS OF USE OF PROBIOTIC BIFIDOBACTERIA FOR COMPANION ANIMALS

(71) Applicants: Mars, Incorporated, McLean, VA (US); Alimentary Health Limited, County Cork (IE)

(72) Inventors: Thomas William-Maxwell Boileau, Galloway, OH (US); Michael Anthony Ceddia, Newburgh, IN (US); Gary Mitchell Davenport, Dayton, OH (US); Barry Pius Kiely, Cork (IE); Liam Diarmuid O'Mahony, Cork (IE); Gregory Dean Sunvold, Lewisburg, OH (US); Mark Alan Tetrick, Dayton, OH (US); Robert Jason Vickers, Dayton, OH (US)

(73) Assignee: Mars, Incorporated, McLean, VA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/517,196

(22) Filed: Oct. 17, 2014

(65) Prior Publication Data

US 2015/0190437 A1 Jul. 9, 2015

Related U.S. Application Data

(63) Continuation of application No. 11/012,947, filed on Dec. 15, 2004, now Pat. No. 8,877,178.

(60) Provisional application No. 60/531,597, filed on Dec. 19, 2003.

(51) Int. Cl.
| | | |
|---|---|---|
| A61K 35/00 | (2006.01) | |
| A61K 35/745 | (2015.01) | |
| A23K 10/18 | (2016.01) | |
| A23K 50/40 | (2016.01) | |
| C12N 1/20 | (2006.01) | |

(52) U.S. Cl.
CPC ............ *A61K 35/745* (2013.01); *A23K 10/18* (2016.05); *A23K 50/40* (2016.05); *C12N 1/20* (2013.01); *A23Y 2300/00* (2013.01); *A61K 2035/115* (2013.01); *Y10S 435/822* (2013.01)

(58) Field of Classification Search
CPC .... A23K 1/009; A23K 1/1846; A23K 1/1853; A23K 1/1866; A23K 1/008; A23K 1/186; A23K 1/164; A23K 10/18; A23K 50/40; A23K 50/42; A23K 50/48; A23K 10/16; A23K 50/45; A23K 20/158; C12N 1/20; C12N 1/61; C12N 35/745; A61K 2035/115; A61K 35/74; A61K 35/747; A61K 35/745; A61K 35/61; C12R 1/01; C12R 1/225; A23L 1/3014; A23L 1/3002
See application file for complete search history.

(56) References Cited

U.S. PATENT DOCUMENTS

| | | |
|---|---|---|
| 571,521 A | 11/1896 | Heberline et al. |
| 1,086,936 A | 2/1914 | Pounder et al. |
| 1,503,094 A | 7/1924 | Cramer |
| 2,473,773 A | 6/1949 | West |
| 2,540,979 A | 2/1951 | Clymer et al. |
| 2,641,548 A | 6/1953 | Heinrich |
| 3,320,130 A | 5/1967 | Henry |
| 3,398,001 A | 8/1968 | Benson |
| 3,429,426 A | 2/1969 | Wolf et al. |
| 3,431,338 A | 3/1969 | Munzel |
| 3,677,898 A | 7/1972 | Mitsugi et al. |
| 3,897,572 A | 7/1975 | Riggs et al. |
| 3,898,132 A | 8/1975 | Heltrick |
| 3,931,885 A | 1/1976 | Nahill et al. |
| 3,957,974 A | 5/1976 | Hata |
| 3,984,576 A | 10/1976 | Burkwall et al. |
| 3,989,822 A | 11/1976 | Whistler |
| 4,248,857 A | 2/1981 | DeNeale et al. |
| 4,295,567 A | 10/1981 | Knudsen et al. |
| 4,314,995 A | 2/1982 | Hata et al. |
| 4,332,790 A | 6/1982 | Sozzi et al. |
| 4,338,346 A | 7/1982 | Brand |
| 4,399,163 A | 8/1983 | Brennan et al. |
| 4,403,623 A | 9/1983 | Mark |
| 4,411,925 A | 10/1983 | Brennan et al. |
| 4,423,029 A | 12/1983 | Rizzi |

(Continued)

FOREIGN PATENT DOCUMENTS

| | | |
|---|---|---|
| AU | 199642145 | 8/1996 |
| AU | 199928098 | 7/1999 |

(Continued)

OTHER PUBLICATIONS

Scardovi, et al., "Deoxyribonucleic Acid Homology Relationships Among Species of the Genus *Bifidobacterium*", Int. J. Syst. Bacteriol., vol. 21, pp. 276-294, 1971.

Scardovi, "Irregular Nonsporing Gram-Positive Rods", Genus *Bifidobacterium* Orla Jensen, 1924, 472.

Schmitt, et al., "The Immunostimulatory Function of IL-12 in T-Helper Cell Development and its Regulation by TGF-B, IFN-y and IL-4", Chem. Immunet Basel Karger, 1997, vol. 68, pp. 70-85.

Schrek, et al., "Characterizatoin of the B Lymphocyte Response to Pokeweed Mitogen", Annals of Clinical and Laboratory Science, vol. 12, Issue 6, pp. 455-462.

(Continued)

*Primary Examiner* — Debbie K Ware
(74) *Attorney, Agent, or Firm* — Mars, Incorporated; Colleen Kramer

(57) ABSTRACT

According to the present invention there are provided methods of regulating the immune system of a companion animal and methods of improving the digestion of a companion animal, wherein each of said methods comprises administering to a companion animal a probiotic bacteria strain of the genus *Bifidobacteria*.

18 Claims, No Drawings

(56) References Cited

U.S. PATENT DOCUMENTS

| | | |
|---|---|---|
| 4,434,231 A | 2/1984 | Jung |
| 4,518,696 A | 5/1985 | Gehrmann et al. |
| 4,592,748 A | 6/1986 | Jost |
| 4,647,453 A | 3/1987 | Meisner |
| 4,736,849 A | 4/1988 | Leonard et al. |
| 4,764,389 A | 8/1988 | LaBarge |
| 4,767,623 A | 8/1988 | Conway et al. |
| 4,781,939 A | 11/1988 | Martin et al. |
| 4,786,507 A | 11/1988 | Schmidt |
| 4,797,289 A | 1/1989 | Reddy |
| 4,806,368 A | 2/1989 | Reddy |
| 4,808,626 A | 2/1989 | Friedman et al. |
| 4,814,193 A | 3/1989 | Shenouda et al. |
| 4,816,259 A | 3/1989 | Matthews et al. |
| 4,859,377 A | 8/1989 | Shasha et al. |
| 4,889,238 A | 12/1989 | Batchelor |
| 4,935,247 A | 6/1990 | Martila et al. |
| 4,937,077 A | 6/1990 | Deetz, III |
| 5,032,399 A | 7/1991 | Gorbach et al. |
| 5,096,717 A | 3/1992 | Wirth et al. |
| 5,132,137 A | 7/1992 | Reimann |
| 5,160,745 A | 11/1992 | DeLuca et al. |
| 5,171,580 A | 12/1992 | Imartino et al. |
| 5,176,911 A | 1/1993 | Tosi et al. |
| 5,286,495 A | 2/1994 | Batich et al. |
| 5,292,657 A | 3/1994 | Rutherford |
| 5,296,233 A | 3/1994 | Batista et al. |
| 5,322,686 A | 6/1994 | Grahn et al. |
| 5,344,824 A | 9/1994 | Ohkuma et al. |
| 5,389,389 A | 2/1995 | Beck |
| 5,413,960 A | 5/1995 | Dobrogosz et al. |
| 5,445,828 A | 8/1995 | Pozzi et al. |
| 5,451,400 A | 9/1995 | Stern et al. |
| 5,474,932 A | 12/1995 | Bengmark et al. |
| 5,484,721 A | 1/1996 | Ors et al. |
| 5,501,857 A | 3/1996 | Zimmer |
| 5,501,868 A | 3/1996 | Collings |
| 5,516,684 A | 5/1996 | Saito et al. |
| 5,518,733 A | 5/1996 | Lamothe et al. |
| 5,531,988 A | 7/1996 | Paul |
| 5,538,743 A | 7/1996 | Heinemann et al. |
| 5,540,945 A | 7/1996 | Ikushima |
| 5,569,634 A | 10/1996 | Miller et al. |
| 5,578,302 A | 11/1996 | Brassart et al. |
| 5,582,643 A | 12/1996 | Takei et al. |
| 5,603,930 A | 2/1997 | Brassart |
| 5,629,017 A | 5/1997 | Pozzi et al. |
| 5,633,012 A | 5/1997 | Ford |
| 5,645,830 A | 7/1997 | Reid |
| 5,698,437 A | 12/1997 | Matsuda et al. |
| 5,726,161 A | 3/1998 | Whistler |
| 5,728,380 A | 3/1998 | Allen et al. |
| 5,733,540 A | 3/1998 | Lee |
| 5,756,088 A | 5/1998 | Matsuura et al. |
| 5,766,520 A | 6/1998 | Bronshtein |
| 5,785,990 A | 7/1998 | Langreher |
| 5,814,338 A | 9/1998 | Veronesi |
| 5,824,779 A | 10/1998 | Koegel et al. |
| 5,849,327 A | 12/1998 | Berliner et al. |
| 5,853,697 A | 12/1998 | Strober et al. |
| 5,854,067 A | 12/1998 | Newgard et al. |
| 5,858,356 A | 1/1999 | Wolf et al. |
| 5,871,794 A | 2/1999 | Brito |
| 5,871,802 A | 2/1999 | Gao |
| 5,894,029 A | 4/1999 | Brown et al. |
| 5,910,447 A | 6/1999 | Lawrence et al. |
| 5,932,258 A | 8/1999 | Sunvold |
| 5,939,117 A | 8/1999 | Chen et al. |
| 5,952,021 A | 9/1999 | Santus |
| 5,952,033 A | 9/1999 | Anantharaman et al. |
| 5,962,043 A | 10/1999 | Jones |
| 5,968,569 A | 10/1999 | Cavadini et al. |
| 5,976,579 A | 11/1999 | McLean |
| 6,007,808 A | 12/1999 | DeHaen et al. |
| 6,010,725 A | 1/2000 | Meister et al. |
| 6,033,888 A | 3/2000 | Batich et al. |
| 6,042,857 A | 3/2000 | Jones et al. |
| 6,063,414 A | 5/2000 | Jones et al. |
| 6,077,530 A | 6/2000 | Weinstein et al. |
| 6,080,401 A | 6/2000 | Reddy et al. |
| 6,083,520 A | 7/2000 | Toneby |
| 6,117,477 A | 9/2000 | Paluch et al. |
| 6,133,323 A | 10/2000 | Hayek |
| 6,156,355 A | 12/2000 | Shields et al. |
| 6,190,591 B1 | 2/2001 | Van Lengerich |
| 6,214,336 B1 | 4/2001 | Bukowska et al. |
| 6,254,886 B1 | 7/2001 | Fusca et al. |
| 6,277,370 B1 | 8/2001 | Vavaliere Ved Vesely et al. |
| 6,309,666 B1 | 10/2001 | Hatano et al. |
| 6,310,090 B1 | 10/2001 | Hayek |
| 6,355,242 B1 | 3/2002 | Allison et al. |
| 6,358,555 B1 | 3/2002 | Takahashi |
| 6,365,148 B1 | 4/2002 | Kim et al. |
| 6,375,956 B1 | 4/2002 | Hermelin et al. |
| 6,394,803 B1 | 5/2002 | Salz et al. |
| 6,406,853 B1 | 6/2002 | Spindler |
| 6,451,341 B1 | 9/2002 | Slaga et al. |
| 6,500,463 B1 | 12/2002 | Van Lengerich |
| 6,506,389 B2 | 1/2003 | Leer et al. |
| 6,537,544 B1 | 3/2003 | Johansson et al. |
| 6,544,568 B2 | 4/2003 | La Droitte et al. |
| 6,562,336 B2 | 5/2003 | De Simone |
| 6,572,854 B1 | 6/2003 | De Simone |
| 6,586,027 B2 | 7/2003 | Axelrod et al. |
| 6,588,180 B2 | 7/2003 | Heath |
| 6,592,863 B2 | 7/2003 | Fuchs et al. |
| 6,596,946 B2 | 7/2003 | Chapnick et al. |
| 6,607,905 B1 | 8/2003 | Luquet |
| 6,620,440 B1 | 9/2003 | Hsia |
| 6,624,162 B2 | 9/2003 | Uchida et al. |
| 6,681,935 B1 | 1/2004 | Lewis |
| 6,713,083 B1 | 3/2004 | McGregor et al. |
| 6,723,358 B1 | 4/2004 | Van Lengerich |
| 6,733,795 B2 | 5/2004 | Piccirilli et al. |
| 6,737,089 B2 | 5/2004 | Wadsworth et al. |
| 6,746,672 B2 | 6/2004 | O'Sullivan |
| 6,767,573 B1 | 7/2004 | Dixon et al. |
| 6,780,433 B2 | 8/2004 | Cochran et al. |
| 6,797,266 B2 | 9/2004 | Naidu |
| 6,802,422 B2 | 10/2004 | Kalvelage et al. |
| 6,827,957 B2 | 12/2004 | Paluch et al. |
| 6,835,376 B1 | 12/2004 | Neeser et al. |
| 6,835,397 B2 | 12/2004 | Lee et al. |
| 6,893,662 B2 | 5/2005 | Dittmar et al. |
| 6,896,914 B2 | 5/2005 | Chapnick et al. |
| 6,905,679 B1 | 6/2005 | Schiffrin et al. |
| 6,911,217 B1 | 6/2005 | Gren et al. |
| 6,932,990 B2 | 8/2005 | Konishi et al. |
| 6,939,560 B2 | 9/2005 | Shen et al. |
| 6,974,594 B2 | 12/2005 | Ko et al. |
| 6,979,675 B2 | 12/2005 | Tidmarsh |
| 6,991,819 B2 | 1/2006 | Pannevis et al. |
| 7,008,648 B2 | 3/2006 | Corley et al. |
| 7,029,669 B1 | 4/2006 | Reniero et al. |
| 7,037,708 B1 | 5/2006 | Runge et al. |
| 7,052,588 B2 | 5/2006 | Gu et al. |
| 7,081,478 B2 | 7/2006 | Hauptmann et al. |
| 7,097,831 B1 | 8/2006 | Bengs et al. |
| 7,115,297 B2 | 10/2006 | Stillman et al. |
| 7,122,370 B2 | 10/2006 | Porubcan |
| RE39,436 E | 12/2006 | Spindler et al. |
| 7,150,986 B2 | 12/2006 | Kato et al. |
| 7,179,460 B2 | 2/2007 | Dennin et al. |
| 7,186,545 B2 | 3/2007 | Collins et al. |
| 7,189,390 B2 | 3/2007 | Zink et al. |
| 7,201,923 B1 | 4/2007 | Van Lengerich et al. |
| 7,229,818 B2 | 6/2007 | Porubcan |
| 7,235,276 B2 | 6/2007 | Allen et al. |
| 7,235,395 B2 | 6/2007 | Stadler et al. |
| 7,381,406 B2 | 6/2008 | Zink et al. |
| 7,390,519 B2 | 6/2008 | Collins et al. |
| 7,427,398 B2 | 9/2008 | Baillon et al. |
| 7,498,162 B2 | 3/2009 | Germond et al. |
| 7,544,497 B2 | 6/2009 | Sinclair et al. |

(56) References Cited

U.S. PATENT DOCUMENTS

| | | |
|---|---|---|
| 7,547,527 B2 | 6/2009 | Baur et al. |
| 7,550,285 B2 | 6/2009 | Schiffrin et al. |
| 7,579,030 B2 | 8/2009 | Domingues et al. |
| 7,604,809 B2 | 10/2009 | Postaire et al. |
| 7,647,098 B2 | 1/2010 | Prichep |
| 7,666,459 B2 | 2/2010 | Hayek et al. |
| 7,674,808 B2 | 3/2010 | Bueno Calderon et al. |
| 7,687,077 B2 | 3/2010 | Khoo |
| 7,687,085 B2 | 3/2010 | Hayashi et al. |
| 7,700,141 B2 | 4/2010 | Baillon et al. |
| 7,700,315 B2 | 4/2010 | Arigoni et al. |
| 7,771,982 B2 | 8/2010 | Zink et al. |
| 7,785,635 B1 | 8/2010 | Boileau et al. |
| 7,795,227 B2 | 9/2010 | Kriegler et al. |
| 7,816,547 B2 | 10/2010 | Msika et al. |
| 7,833,554 B2 | 11/2010 | Piccirilli et al. |
| 7,838,057 B2 | 11/2010 | Schmidt et al. |
| 7,842,329 B2 | 11/2010 | Saylock et al. |
| 7,897,579 B2 | 3/2011 | Piccirilli et al. |
| 7,906,112 B2 | 3/2011 | Boileau et al. |
| 7,910,144 B2 | 3/2011 | Ballevre et al. |
| 7,935,334 B2 | 5/2011 | Lin |
| 7,960,605 B2 | 6/2011 | Zhao-Wilson |
| 7,998,473 B2 * | 8/2011 | Boileau .................. A23K 1/009 424/93.2 |
| 8,030,279 B2 | 10/2011 | Joullie |
| 8,034,601 B2 * | 10/2011 | Boileau ................ A23C 9/1234 424/93.4 |
| 8,057,840 B2 | 11/2011 | Harrison et al. |
| 8,092,608 B2 | 1/2012 | Rochat et al. |
| 8,101,170 B2 | 1/2012 | Plail et al. |
| 8,142,810 B2 | 3/2012 | Sunvold |
| 8,263,146 B2 | 9/2012 | Bengtsson-Riveros et al. |
| 8,313,757 B2 | 11/2012 | Van Lengerich |
| 8,329,190 B2 | 12/2012 | Vidal et al. |
| 8,349,377 B2 | 1/2013 | Piccirilli et al. |
| 8,394,370 B2 | 3/2013 | Garcia-Rodenas et al. |
| 8,486,389 B2 | 7/2013 | Sidhu et al. |
| 8,524,304 B2 | 9/2013 | Prakash et al. |
| 8,540,980 B2 | 9/2013 | London et al. |
| 8,557,764 B2 | 10/2013 | Newell et al. |
| 8,563,522 B2 | 10/2013 | Pitha et al. |
| 8,637,495 B2 | 1/2014 | Waldron et al. |
| 8,663,729 B2 | 3/2014 | Hayek et al. |
| 8,691,303 B2 | 4/2014 | Sunvold et al. |
| 8,722,112 B2 | 5/2014 | Zicker et al. |
| 8,728,559 B2 | 5/2014 | Hayek et al. |
| 8,771,675 B2 | 7/2014 | Zink et al. |
| 8,802,158 B2 | 8/2014 | Boileau et al. |
| 8,802,179 B2 | 8/2014 | Miller |
| 8,808,770 B2 | 8/2014 | Henderson et al. |
| 8,809,035 B2 * | 8/2014 | Boileau .................. A23K 1/008 424/93.2 |
| 8,865,197 B2 | 10/2014 | Tandler et al. |
| 8,877,178 B2 * | 11/2014 | Boileau .................. A23K 1/009 424/93.4 |
| 8,894,991 B2 | 11/2014 | Boileau et al. |
| 8,900,569 B2 | 12/2014 | Boileau et al. |
| 8,916,145 B2 | 12/2014 | Mercenier et al. |
| 8,962,007 B2 | 2/2015 | Perez-Camargo et al. |
| 9,023,810 B2 | 5/2015 | Piccirilli et al. |
| 9,089,576 B2 | 7/2015 | Piccirilli et al. |
| 9,119,843 B2 | 9/2015 | Chen et al. |
| 9,192,177 B2 | 11/2015 | Boileau et al. |
| 2002/0006432 A1 * | 1/2002 | Collins ................ A23C 9/1234 424/439 |
| 2002/0022019 A1 | 2/2002 | Laulund |
| 2002/0035071 A1 | 3/2002 | Pitha et al. |
| 2002/0119237 A1 | 8/2002 | Hevey |
| 2002/0127211 A1 | 9/2002 | Brassart et al. |
| 2003/0049240 A1 | 3/2003 | Bellevre et al. |
| 2003/0060503 A1 | 3/2003 | Hamilton |
| 2003/0104090 A1 | 6/2003 | Levy et al. |
| 2003/0113306 A1 | 6/2003 | Collins et al. |
| 2003/0143293 A1 | 7/2003 | Shushunov |
| 2003/0157166 A1 | 8/2003 | Chen et al. |
| 2003/0170217 A1 | 9/2003 | Collins et al. |
| 2003/0170355 A1 | 9/2003 | Glazier et al. |
| 2003/0190314 A1 | 10/2003 | Campbell et al. |
| 2003/0194423 A1 | 10/2003 | Torney et al. |
| 2004/0001817 A1 | 1/2004 | Giampapa et al. |
| 2004/0047896 A1 | 3/2004 | Malnoe et al. |
| 2004/0161422 A1 | 8/2004 | Ranganathan |
| 2004/0167229 A1 | 8/2004 | Bakker-Arkema et al. |
| 2004/0234579 A1 | 11/2004 | Finke |
| 2004/0253357 A1 | 12/2004 | De Zarate |
| 2004/0265279 A1 | 12/2004 | Dinan et al. |
| 2005/0013849 A1 | 1/2005 | Lemaure et al. |
| 2005/0074519 A1 | 4/2005 | Bartnick et al. |
| 2005/0079244 A1 | 4/2005 | Giffard et al. |
| 2005/0084479 A1 | 4/2005 | Corthesy-Theulay et al. |
| 2005/0100617 A1 | 5/2005 | Malnoe et al. |
| 2005/0106131 A1 | 5/2005 | Breton et al. |
| 2005/0112259 A1 | 5/2005 | Qvyjt |
| 2005/0152884 A1 | 7/2005 | Boileau et al. |
| 2005/0153018 A1 | 7/2005 | Ubbink et al. |
| 2005/0164978 A1 | 7/2005 | Chapnick et al. |
| 2005/0180961 A1 | 8/2005 | Pequet et al. |
| 2005/0208163 A1 | 9/2005 | Brovelli et al. |
| 2005/0249837 A1 | 11/2005 | Massimino et al. |
| 2005/0266438 A1 | 12/2005 | Spindler |
| 2005/0281910 A1 | 12/2005 | Schiffrin et al. |
| 2006/0002909 A1 | 1/2006 | Takeda |
| 2006/0008511 A1 | 1/2006 | Lin et al. |
| 2006/0070895 A1 | 4/2006 | Khawaja |
| 2006/0099196 A1 | 5/2006 | Breton et al. |
| 2006/0100162 A1 | 5/2006 | Pitha et al. |
| 2006/0116330 A1 | 6/2006 | Pitha et al. |
| 2006/0121015 A1 | 6/2006 | Collins et al. |
| 2006/0147962 A1 | 7/2006 | Jones et al. |
| 2006/0165670 A1 | 7/2006 | Berr et al. |
| 2006/0228448 A1 | 10/2006 | Boileau et al. |
| 2006/0228459 A1 | 10/2006 | Tribelhorn et al. |
| 2006/0263416 A1 | 11/2006 | Brent, Jr. |
| 2007/0009577 A1 | 1/2007 | Mankovitz |
| 2007/0031441 A1 | 2/2007 | Collins et al. |
| 2007/0082107 A1 | 4/2007 | Almutis et al. |
| 2007/0098744 A1 | 5/2007 | Knorr et al. |
| 2007/0116853 A1 | 5/2007 | Krohn et al. |
| 2007/0122531 A1 | 5/2007 | Considini |
| 2007/0123460 A1 | 5/2007 | Chang et al. |
| 2007/0129428 A1 | 6/2007 | Richelle et al. |
| 2007/0149466 A1 | 6/2007 | Milburn et al. |
| 2007/0160589 A1 | 7/2007 | Mattson et al. |
| 2007/0166295 A1 | 7/2007 | Schildgen et al. |
| 2007/0178078 A1 | 8/2007 | Khoo |
| 2007/0190171 A1 | 8/2007 | Yamka et al. |
| 2007/0218164 A1 | 9/2007 | Stojanovic |
| 2007/0231371 A1 | 10/2007 | Pan et al. |
| 2007/0231414 A1 | 10/2007 | Aoki et al. |
| 2007/0269515 A1 | 11/2007 | Henriksen et al. |
| 2007/0269553 A1 | 11/2007 | Le et al. |
| 2007/0280964 A1 | 12/2007 | Knorr et al. |
| 2007/0286935 A1 | 12/2007 | Grigorov et al. |
| 2008/0044481 A1 | 2/2008 | Harel |
| 2008/0050354 A1 | 2/2008 | Garault et al. |
| 2008/0050355 A1 | 2/2008 | Vaslin |
| 2008/0053490 A1 | 3/2008 | Clark et al. |
| 2008/0107699 A1 | 5/2008 | Spigelman et al. |
| 2008/0145341 A1 | 6/2008 | Myatt et al. |
| 2008/0214479 A1 | 9/2008 | Pitha et al. |
| 2008/0241226 A1 | 10/2008 | Abeln et al. |
| 2008/0260696 A1 | 10/2008 | Massimino et al. |
| 2008/0260866 A1 | 10/2008 | Massimino et al. |
| 2008/0279786 A1 | 11/2008 | Cash |
| 2008/0280274 A1 | 11/2008 | Friesen et al. |
| 2008/0305210 A1 | 12/2008 | Petersen |
| 2008/0311226 A1 | 12/2008 | Yamka et al. |
| 2008/0317905 A1 | 12/2008 | Yamka et al. |
| 2009/0252834 A1 | 10/2009 | Hayek et al. |
| 2009/0263542 A1 | 10/2009 | Lin et al. |
| 2009/0274796 A1 | 11/2009 | Yamka et al. |
| 2009/0324761 A1 | 12/2009 | Khoo et al. |

(56) References Cited

U.S. PATENT DOCUMENTS

| | | |
|---|---|---|
| 2010/0003369 A1 | 1/2010 | Ter Haar et al. |
| 2010/0112003 A1 | 5/2010 | Collins et al. |
| 2010/0158070 A1 | 6/2010 | Steinboeck et al. |
| 2010/0203225 A1 | 8/2010 | Kerr et al. |
| 2010/0233320 A1 | 9/2010 | Sunvold et al. |
| 2010/0316769 A1 | 12/2010 | Czarnecki-Maulden et al. |
| 2011/0117068 A1 | 5/2011 | Lang et al. |
| 2011/0274676 A1 | 11/2011 | Farmer et al. |
| 2012/0115798 A1 | 5/2012 | Massimino et al. |
| 2012/0282373 A1 | 11/2012 | Luhadiya et al. |
| 2012/0283197 A1 | 11/2012 | Luhadiya et al. |
| 2013/0183255 A1 | 7/2013 | Saunois et al. |
| 2014/0274920 A1 | 9/2014 | Davenport |
| 2014/0348975 A1 | 11/2014 | Davenport et al. |
| 2014/0348986 A1 | 11/2014 | Beyer et al. |
| 2014/0349002 A1 | 11/2014 | Beyer |
| 2015/0132420 A1 | 5/2015 | Martinez-Serna Villagran et al. |
| 2015/0208679 A1 | 7/2015 | Mir et al. |

FOREIGN PATENT DOCUMENTS

| | | |
|---|---|---|
| CA | 1300538 | 5/1992 |
| CA | 2093287 | 10/1993 |
| CA | 2256256 | 6/2000 |
| CA | 2569249 | 11/2005 |
| DE | 3715070 | 11/1988 |
| DE | 4018392 | 12/1991 |
| DE | 10217970 | 11/2003 |
| EP | 0168112 | 1/1986 |
| EP | 0181170 | 5/1986 |
| EP | 0212746 | 3/1987 |
| EP | 0212747 | 3/1987 |
| EP | 0298605 | 1/1989 |
| EP | 0391416 | 10/1990 |
| EP | 0399819 | 11/1990 |
| EP | 0563934 | 10/1993 |
| EP | 0627173 | 12/1994 |
| EP | 0850569 | 7/1998 |
| EP | 1547466 | 6/2005 |
| EP | 1637041 | 3/2006 |
| EP | 1806056 | 7/2007 |
| EP | 1806057 | 7/2007 |
| FR | 2615203 | 11/1988 |
| FR | 2663198 | 12/1991 |
| GB | 1190387 | 5/1970 |
| GB | 1503094 | * 4/1976 |
| GB | 1595054 | 8/1981 |
| GB | 2241421 | 9/1990 |
| GB | 2252228 | 8/1992 |
| JP | S59213368 | 12/1984 |
| JP | S6024153 | 2/1985 |
| JP | S62201823 | 9/1987 |
| JP | 03076561 | 4/1991 |
| JP | H06256170 | 9/1994 |
| JP | H08242763 | 9/1996 |
| JP | 2000191519 | 7/2000 |
| JP | 2001278781 | 10/2001 |
| JP | 2001309753 | 11/2001 |
| JP | 2007117083 | 11/2001 |
| JP | 1995378530 | 8/2003 |
| JP | 2004173675 | 6/2004 |
| JP | 2006055145 | 3/2006 |
| KR | 20020050048 | 6/2002 |
| KR | 20040024774 | 3/2004 |
| RU | 2086248 | 8/1997 |
| RU | 2123343 | 12/1998 |
| RU | 2388320 | 5/2010 |
| RU | 2407401 | 12/2010 |
| WO | 8808452 | 11/1988 |
| WO | 8905849 | 6/1989 |
| WO | 9001335 | 2/1990 |
| WO | 9117672 | 11/1991 |
| WO | 9302558 | 2/1993 |
| WO | 9404180 | 3/1994 |
| WO | 9421284 | 9/1994 |
| WO | 9503809 | 2/1995 |
| WO | 9507090 | 3/1995 |
| WO | 9709448 | 3/1997 |
| WO | 9716198 | 5/1997 |
| WO | 9720577 | 6/1997 |
| WO | 9819668 | 5/1998 |
| WO | 9827967 | 7/1998 |
| WO | 9854982 | 12/1998 |
| WO | 9909839 | 3/1999 |
| WO | 9930576 | 6/1999 |
| WO | 9952511 | 10/1999 |
| WO | 0006127 | 2/2000 |
| WO | 0112164 | 2/2001 |
| WO | 01/90311 | 11/2001 |
| WO | 03045356 | 6/2003 |
| WO | 03/075676 | 9/2003 |
| WO | 2004074496 | 9/2004 |
| WO | 2004100670 | 11/2004 |
| WO | 2005070232 | 8/2005 |
| WO | 2005092116 | 10/2005 |
| WO | 2007060539 | 5/2007 |
| WO | 2007/126990 | 11/2007 |
| WO | 2007137808 | 12/2007 |

OTHER PUBLICATIONS

Scrimshaw, et al., "Interactions of Nutrition and Infection", Am. J. Med. Sci., 1959, 237: 367-403.

Scruel, et al., "Interference of D-Mannoheptuloase with D-Glucose phosphorylation, Metabolism, and Functional Effects: Comparison between Liver, Parotid Cells and Pancreatic Islets", Molecular and Cellular Biochemistry, 187, pp. 113-120, 1998.

Sener, et al., "D-Mannoheptulose Uptake and Its Metabolic and Secretory Effects in Human Pancreatic Islets", International Journal of Molecular Medicine, 6:617-620, 2000.

Sener, et al., "Environmental Modulation of D-Fructose Insulinotropic Action", Acta Diabetol, 1998, 35, pp. 74-76.

Shanahan, et al., "Genes, Bacteria and T Cells: Ingredients for Inflammatory Bowel Disease", Selected Summaries, Gastroenterology, 1998, 115, pp. 1595-1600.

Shanahan, "The Intestinal Immune System", Physiology of the Gastrointestinal Tract, 3rd. ed., 1994.

Shaw, et al., "High Performance Liquid Chromatographic Analysis of d-manno-heptulose, perseitol, glucose and Fructose in Avocado Cultivars", J. Agric. Food Chem., 1980, 28, 279-382.

Shimada, "Significance of 1,5-Anhydro-D-Glucitol in Diabetes Mellitus Management", Sangyo Igaku, 1994, 36(3), pp. 448-449.

Silva De Ruiz, et al., "Effect of Lactobacilli and Antibiotics on E. coli Urinary Infections in Mice", Biol. Pharm. Bull., 1996, 19(1): 88-93.

Simon, et al., "Insulin and Proinsulin Secretion and Action", Israel J. Med. Sci., vol. 8, No. 6, Jun. 1972.

Simon, et al., "Metabolism of Mannoheptulose in the Rat. I. Diabetogenic Action", Arch. Biochem. Biophys., 69, pp. 592-601 (1957).

Simons, et al., "2-deoxy-D-glucose (2DG) Enhances Cispalatin Cytotoxicity in Human Head and Neck Cancer Cells Via Metabolic Oxidative Stress", Free Radical Biology and Medicine, vol. 41, No. 1, Nov. 15, 2006, pp. S112-S113.

Simpson, et al., "Genomic Diversity and Relatedness of Bifidobacteria isolated from a Porcine Cecum", Journal of Bacteriology, Apr. 2003, vol. 185, pp. 2571-2581.

Snow Brand Milk Products, "Enteric Capsules—comprising Core Contaiing Drug etc. AndCoating of Hardened Oil of M. Pt. Higher than Body Temp and Disintegrated by Lipase in Intestine", SNOW, Mar. 31, 1986.

Sols, et al., "Substrate Specificity of Brain Hexokinase", Biol. Chem. 210, pp. 581-595 (1954).

Soudeyns, et al., "The Moving Target: Mechanisms of HIV Persistance During Primary Infection", Immunology Today, Oct. 1999.

SS Pharmaceutical KK, "Tablets Containing Double-Coated Granules-Obtained by Coating with Insol. Polymer, Enteric Polymer and/or Waces, Then Further Coating with Water or Acid-Soluble Polymer", SSSE, Aug. 18, 1988.

(56) References Cited

OTHER PUBLICATIONS

Stagg, et al., "The Dendritic Cell: Its Role in Intestinal Inflammation and Relationship with Gut Bacteria", www.Gutjnl.com.
Stallmach, et al., "Induction and Modulation of Gastrointestinal Inflammation", Trends Immunology Today, Oct. 1998, vol. 19, No. 10, pp. 438-441.
Strober, et al., "Reciprocal IFN-Gamma and TFG-Beta Responses Regulate the Occurrence of Mucosal Inflammation", Immunol. Today, Feb. 18, 1997, 2, pp. 61-64.
Sung, et al., "The Sphincter of Oddi is a Boundary for Bacterial Colonization in the Feline Biliary Tract", Microbial Ecology in Health and Disease, 1990, vol. 3, pp. 199-207.
Sunvold, et al., "Dietary Fiber for Dogs: IV. In Vitro Fermentation of Selected Fiber Sources by Dog Fecal Inoculum and In Vivo Digestion and Metabolism of Fiber-Supplemented Diets", J. Anim. Sci., vol. 73, 1995, 1099-1109.
Sutton, et al., "Considerations for Successful Development and Launch of Personalized Nutrigenomic Foods", Mutation Research, vol. 622, No. 1-2, Aug. 8, 2007, pp. 117-121.
Takayanagi, J. Nippon Med. Sch., 2003, vol. 70, No. 1, p. 71 (with machine translation), 2003, 71.
Takeda Chemical IND KK, "Dry Coated Tablet—Comprises Core Tablets Containing Enzyme Prepn in Enteric Films Within Outer Shell", TAKE, May 10, 1982.
Tesfay, et al., "Anti-Oxidant Levels in Various Tissues During the Maturation of "Hass" Avocado", Journal of Horticultural Science and Biotechnology, 85(2): 106-112.
Tomomatsu, "Health Effects of Oligosaccharides", 1994, Food Technology, 48, pp. 61-65.
Trovatelli, et al., "Presence of Bifidobacteria in the Rumen of Calves Fed Different Rations", Appl. Environ. Microbiol., 1976, vol. 32(4), pp. 470-473.
Valente, et al., "Immunologic Function in the Elderly After Injury—The Neutrophil and Innate Immunity", The Journal of Trauma Injury, Infection and Critical Care, vol. 67, No. 5, pp. 968-974, Nov. 2009.
Van Damme, et al., "The Proportion of Th 1 Cells, Which Prevail in Gut Mucosa, is Decreased in Inflammatory Bowel Syndrome", 2001, Blackwell Science Ltd. Clinical and Experimental Immunology, 125, pp. 383-390.
Vasconcelos, et al., "Antagonistic and Protective Effects Against *Salmonella enterica* Serovar Typhimurium by Lactobacillus murinus in the Digestive Tract of Gnotobiotic Mice", Brazilian Journal of Microbiology (2003) 34 (Supple. 1): 21-24.
Vickers, et al., "Comparison of Fermentation of Selected Fructooligosaccharides and Other Fiber Substrates by Canine Colonic Microflora", AJVR, vol. 62, No. 4, Apr. 2001.
Viktora, et al., "Effect of Ingested Mannoheptulose in Animals and Man", Metabolism, 18(2), 87-102, 1969.
Voet, et al., Biochemistry, John Wiley & Sons, Inc., pp. 1044-1045.
Walker-Bone, et al., "Natural Remedies in the Treatment of Osteoarthritis", Drugs and Aging, 2003, 20(7), pp. 517-526.
Wamelink, et al., "Detection of Transaldolase Deficiency by Quantification of Novel Seven-Carbon Chain Carbohydrate Biomarkers in Urine", J. Inherit. Metab. Dis., (2007), 30, pp. 735-742.
Wan, et al., "Dietary Supplementation with 2-deoxy-d-Glucose Improves Cardiovascular and Neuroendocrine Stress Adaptation in Rats", Am. J. Physiol. Hear. Cir. Physiol, 287: H1186-H1193, 2004.
Wein, et al., "Analyzing a Bioterror Attack on the Food Supply: The Case of Botolinum Toxin in Milk", 2005, The National Academy of Sciences of the USA.
Weindruch, et al., "The Retardation of Aging and Disease by Dietary Restriction", Charles S. Thomas (1988).
Weindruch, "The Retardation of Aging by Caloric Restriction", Toxicol. Pathol., 1996, 24:742.
Willott, et al., "Aging and Presbycusis: Effects on 2-Deoxy-D-Glucose Uptake in the Mouse Auditory Brain Stem in Quiet", Exp. Neurol., vol. 99(3), pp. 615-621.
Winnock, et al., "Correlation Between GABA Release from Rat Islet beta-cells and their Metabolic State", Am. J. Physiol Endocrinol. Metab., 282: E937-E942, 2002.
Wood, et al., "Evidence for Insulin Involvement in Arginine- and Glucose-Induced Hypercalciuria in Rat", J. Nutr., 113, pp. 1561-1567, 1983.
Yaeshima, et al., "Bifidobacterium globosum, Subjective Synonym of Bifidobacterium pseudolongum, and Descrption of *Bifidobacterium pseudolongum* subsp. *pseudolongum* com. nov. and *Bifidobacterium psuedolongum* subsp. *globosum* comb. nov.", Systematic and Applied Microbiology, 1992, vol. 15(3), pp. 380-385.
Yamamoto, et al., "Changes in Behavior and Gene Expression Induced by Caloric Restriction in C57BL/6 Mice", Physiological Genomics, vol. 39, No. 3, Sep. 8, 2009, pp. 227-235.
Yang, et al., "The Role of Voltage-Gated Calcium Channels in Pancreatic [beta]-Cell Physiology and Pathophysiology", Endocrine Reviews, vol. 27, No. 6, Oct. 1, 2006.
Johnston, "Small Intestinal Bacterial Overgrowth", The Veterinary Clinics of North America, Small Animal Practice, Mar. 1999, vol. 29, No. 2, Mar. 1999, pp. 523-550.
Kalani, et al., "Effects of Caloric Restriction and Exercise on Age-Related, Chronic Inflammation Assessed by C-Reactive Protein and Interleukin-6", J. Gerontol. A. Bio. Sci. Med. Sci., vol. 61(3), pp. 211-217 (2006).
Kalant, et al., "Effect of Diet Restriction on Glucose Metabolism and Insulin Responsiveness in Aging Rates", Mechanisms of Aging and Development, 46 (1988) 89-104.
Kappler-Tanudyaya, et al., "Combination of Biotransformation and Chromatography for the Isolation and Purification of Mannoheptulose", Biotechnology J. 2007, 2, 692-699.
Katzmarzyk, "The Metabolic Syndrome: An Introduction", Appl. Physiol. Nutr. Metab., 32, pp. 1-3 (2007).
Kaufman, et al., "Identification and Quantification of *Bifidobacterium* Species Isolated from Food with Genus-Specific 16S rRNA-Targeted Probes by Colony Hybridization and PCR", Appl. Environ. Microbiol., Apr. 1997, vol. 63, pp. 1268-1273.
Kealy, et al., "Effects of Diet Restriction on Life Span and Age-Related Changes in Dogs", JAVMA, vol. 220, No. 9, May 1, 2002.
Kibenge, et al., "Identification of Biochemical Defects in Pancreatic Islets of fa/fa Rats", Obesity Research, 3(2), pp. 171-178, Mar. 1995.
Klain, et al., "Mannoheptulose and Fatty Acid Synthesis in the Rat", The Journal of Nutrition, pp. 473-477, 1974.
Koh, et al., "Effects of Mannoheptulose on Lipid Metabolism of Rats", J. Nutr., vol. 104, pp. 1227-1233, 1974.
Koizumi, et al., "Influences of Dietary Restriction and Age on Liver Enzyme Activities and Lipid Peroxidation in Mice", American Institute of Nutrition, Jul. 1986.
Koizumi, et al., "Influences of Dietary Restriction and Age on Liver Enzyme Activities and Lipid Peroxidation in Mice", J. Nutr., 117: 361-367, 1987.
Kok, et al., "Specific Detection and Analysis of a Probiotic Bifidobacterium Strain in Intact Feces", Applied and Environmental Microbiology, 1996, vol. 62, pp. 3668-3672.
Kudo, et al., "An Electron Microscopic Study on Bifidobacterium Pseudolongum SS-24 with Extracellular Material and Naked Bifidobacterium Thermophilum SS-19", AJAS, vol. 2, No. 3, pp. 444-445, 1989.
Kurata, et aL., "Structural Evaluation of Glucose Analogues on Feeding Elicitation in Rat", Metabolism, vol. 38, No. 1 Jan. 1989: pp. 46-51.
Kyoto, "Sustains-Release Formulation which Floats in Stomach—Comprises Core of Fats and Oils, Coated with Drug Containing Layer of e.g., Agar", KYOT, Jul. 10, 1987.
La Forge, "Absorption and Effect of Ingested Mannoheptulose", Nutrition Reviews, 1969, vol. 27, No. 7, pp. 206-208.
La Forge, "D-Mannoketoheptose, A New Sugar from the Avocado", J. Biol. Chem. 28:511-22, 1917.
Lab Prod Ethiques Ethypharm, "Coated Microgranules Containing a Gastric Proton Pump Inhibitor with Two Hydrophobic Materials, Free from Alkali and any Ionic Surfactant", Derwent Publications Ltd., Ethi., May 21, 1999.

(56) References Cited

OTHER PUBLICATIONS

Lakatos, "Immunology of Inflammatory Bowel Diseases", Acta Physiological Hungarica, vol. 87 (4), pp. 355-372, 2000.
Lane, et al., "2-Deoxy-D-Glucose Feeding in Rats Mimics Physiologic Effects of Calorie Restriction", Journal of Anti-Aging Medicine, vol. 1, No. 4, pp. 327-337, 1998.
Lane, et al., "Calorie Restriction in Nonhuman Primates: Implications for Age-Related Disease Risk", Journal of Anti-Aging Medicine, vol. 1, No. 4, pp. 315-326, 1998.
Lane, et al., "Calorie Restriction Lowers Body Temperature in Rhesus Monkeys, Consistent with a Postulated Anti-Aging Mechanisms in Rodents", PNAS, vol. 93, pp. 4159-4164, Apr. 1996.
Langhans, et al., "Changes in Food Intake and Meal Patterns Following Injection of D-Mannoheptulose in Rats", Behavioral and Neural Biology, 38, pp. 269-286 (1983).
Leblond-Bourget, et al., "16S rRNA and 16S to 23S Internal Transcribed Spacer Sequence Analysis Reveal Inter- and Intraspecific Bifidobacterium Phylogeny", International Journal of Systemic Bacteriology, vol. 46, No. 1, Jan. 1996, pp. 102-111.
Leclercq-Meyer, et al., "Effects of D-mannoheptulose and Its Hexaacetate Ester on Hormonal Secretion From the Perfused Pancreas", International Journal of Molecular Medicine, 2000, vol. 6, pp. 143-152.
Lee, "Medicinal Plant Composition Suitable for Each Blood Type", WPI/THOMSON, vol. 2004, No. 46, Mar. 22, 2004.
Libby, "Inflammatory mechanisms: the molecular basis of inflammation and disease", Nutr. Rev., Dec. 2007, 65 (12 Pt. 2): S140-6.
Liu, et al. "Hass Avocado Carbohydrate Fluctuations. I. Growth and Phenology", J. Amer. Soc. Hort. Sci., 124(6): 671-675, 1999.
Liu, et al. "Hass Avocado Carbohydrate Fluctuations. II. Fruit Growth and Ripening", J. Amer. Soc. Hort. Sci., 124(6): 676-681 (1999).
Liu, et al. "Postulated Physiological Roles of the Seven Carbon Sugars, Mannoheptulose, and perseitol in Avocado", J. Amer. Soc. Hort. Sci., 127(1):108-114, 2002.
Maklashina, et al., "Is Defective Electron Transport at the Hub of Aging", Aging Cell, vol. 3, 21-27, 2004.
Mamula, et al., Gastrointestinal Tract Infections—Chapter 11. 2004, pp. 79-89.
Marteau, et al., "Potential of Using Lactic Acid Bacteria for Therapy and Immunomudulation in Man", FEMS Microbiology Reviews, 12, 1993, pp. 207-220.
Masoro et al., "Dietary Restriction Alters Characteristics of Glucose Fuel Use", Journal of Gerontology, Biological Sciences, 1992, vol. 47, No. 6, B202-B208.
Masoro, "Overview of Caloric Restriction and Aging", Mech. Aging Dev., vol. 126, pp. 913-922 (2005).
Massi, et al., NCBI Genbank Accession No. AB102854, NCBI Genbank (1994).
Mattarelli, et al., "Characterization of the plasmid pVS809 from Bifidobacterium globosum", Microbiologica, 1994, vol. 17, pp. 327-331.
Mattson, et al., "Beneficial Effects of Intermittent Fasting and Caloric Restriction on the Cardiovascular and Cerebrovascular Systems", J. Nutr, Biol. 16, 3:129-137, 2005.
McBrearty, et al., "Probiotic Bifidobacteria and Their Identification Using Molecular Genetic Techniques", Teagasc, Dairy Products Research Centre, Moorepark, Fermoy, Co., Cork, Ireland, Department of Microbiology, University College, Cork Ireland.
McCarthy, et al., "Double Blind Placebo Controlled Trial of Two Probiotic Strains in Interleukin", Gastroenterology, vol. 122, No. 4, suppl., 1, pp. A389-A390, DDW Meeting Abstract, Nr. T962.
McCay, et al., "The Effect of Retarded Growth upon the Length of Life Span and upon the Ultimate Body Size", J. Nutr., vol. 10, pp. 63-79 (1935).
McCracken, et al., "Probiotics and the Immune System", in G. W. Tannock (ed.), Probiotics, a critical review. Horizon Scientific Press, Norfolk, United Kingdom, 1999, p. 85-112.

McGee, et al., "A Synergistic Relationship Between TNF-alpha, IL-1B, and TGF-B1 on IL-6 Secretion by the IEC-6 Intertinal Epithelial Cell Line", Immunology, 1995, 86, pp. 6-11.
McKay, et al., "Review Article: In Vitro Models in Inflammatory Bowel Disease", Aliment Pharmacol. Ther., 1997, 11 (suppl. 3), pp. 70-80.
Medaglini, et al., "Mucosal and Systemic Immune Responses to Recombinant Protein Expressed on the Surface of the Oral Commensal Bacterim *Streptococcus gordonil* after Oral Colonization", Proc. Nat. Acad. Sci. USA, vol. 92, pp. 6868-6872, Jul. 1992 Medical Sciences.
Mentula, et al., "Comparison Between Cultured Small-Intestinal and Fecal Microbiotas in Beagle Dogs", Applied and Environmental Microbiology, Aug. 2005, vol. 71, No. 8, p. 4169-4175.
Mermelstein, "Novel Dryer Uses Refractance Window Principle", Food Technology, 51(10), p. 96, 1997.
Meyer, et al., "Long-Term Caloric Restriction Ameliorates the Decline in Diastolic Function in Humans", J. Am. College of Cardiology, vol. 47(2), pp. 398-402 (2006).
Miller, et al., "2-Deoxy-D-Glucose-Induced Metabolic Stress Enhances Resistance to Listeria monocytogenes Infection in Mice", Physiology & Behavior, vol. 65., No. 3, pp. 535-543, 1998, 1998, 535-543.
Collins, "Probiotics and Man—The Host Microbe Interface", Abstracts, Gastroenterology, vol. 116, No. 4.
Collins, et al., "Selection of Probiotic Strains for Human Applications", Dairy Journal, 8, 1998, 487-490.
Conde, et al., "OeMST2 Encodes a Monosaccharide Transporter Expressed throughout Olive Fruit Maturation", Plant Cell Physiol., 48(9), pp. 1299-1308, 2007.
Cooke, et al., "Role of Estrogens in Adipocyte Development and Function", Exp. Biol. Med., 229:1127-35, 2004.
Crane, et al., "The Non-Competitive Inhibition of Brain Hexokinase by Glucose-6-Phosphate and Related Compounds", Biol. Chem., 210, pp. 597-696 (1954).
Cruzen, et al., "Effects of Caloric Restriction on Cardiovascular Aging in Non-Human Primates and Humans", Clin. Geriatr. Med., vol. 25(4), pp. 733-743, Nov. 2009.
Cullen, et al., "Inhibition of Glucose Metabolism in Pancreatic Cancer Induces Cytotoxicity via Metabolic Oxidative Stress", Gastroenterology, vol. 128, No. 4, sup. 2, Apr. 2005, pp. A483, XP002495963.
De Pergola, "The Adipose Tissue Metabolism: Role of Testosterone and Dehydroepiandrosterone", Int. J. Obesity, 24: S59-S63, 2000.
Dent, et al., "Lactobacillus animalis JCM5670", Database JCM Catalogue, Japan Collection of Microorganisms, 1986, XP002447035.
Donnelly, et al., "Differential Regulation of Il-1 Production in Human Monocytes by IFN-y and IL-4", The Journal of Immunology, vol. 145, pp. 569-575, No. 2, Jul. 15, 1990.
Dreau, et al., "Effects of 2-deoxy-D-glucose Adminstration on Immune Parameters in Mice", Immunopharmacology, vol. 39, Jun. 1, 1998, pp. 201-213, 1998, 201-213.
Dunne, et al., "Probiotics: From Myth to Reality, Demonstration of Functionality in Animal Models of Disease and in Human Clinical Trials", Antonie Van Leeuwenhoek. Jul.-Nov. 1999;76(1-4):279-92.
Eisai, "Sustained-Release Solid Preparation of Zero Order Drug Releasing Profile Comprises Granules Obtainable by Coating Inner Core Containing Xanthine Deriv. Etc, with Film of Hardened Oil", EISA, Dec. 22, 1989.
Ekor, et al., "Protective Effect of the Methanolic Leaf Extract of *Persea americana* (avocado) Against Paracetamol-induced acute Hepatoxicity in Rats", International Journal of Pharmacology, vol. 2, No. 4, Jan. 1, 2006, pp. 416-420 XP001538905.
Ernst, "Avocado-Soybean Unsaponifiables (ASU) for Osteoarthritis—A systemic Review", Clin. Rheumatol., 2003, 22, pp. 285-288.
Facchini, et al., "Insulin Resistance as a Predictor of Age-Related Diseases", The Journal of Clinical Endocrinology & Metabolism, 86(8): 3574-3578.

(56) References Cited

OTHER PUBLICATIONS

Fajans, et al., "Stimulation of Insulin Release in the Dog by a Nonmetabolizable Amino Acid. Comparison with Leucine and Arginine", J. of Clinical Endocrinology and Metabolism, 33(1) 35-41, Jul. 1971.

Favier et al., "Fecal B-D-Galactosidase Production and Bifidobacteria are Decreased in Crohn's Disease", Digestive Diseases and Sciences, vol. 42, No. 4, Apr. 1997, pp. 817-822.

Fishbein, et al., "Biological Effects of Dietary Restriction", Springer-Verlag, 1991.

Fontana, et al., "Long-term Calorie Restriction is Highly Effective in Reducing the Risk for Artherosclerosis in Humans", PNAS, vol. 101(17), pp. 6659-6663 (2004).

Francesconi, et al., "5-Thio-D-Glucose: Hypothermic Responses in Mice", Am. J. Physiology, 239(3), R214-R218.

Frech, et al., "The Utility of Nutraceuticals in the Treatment of Osteoarthritis", Current Rheumatology Reports, 2007, 9, pp. 25-30.

Freund, "Capsule Containing Useful Enteric Bacteria—includes Hydrophobic Layer Non-fluid at Room Temp Isolating Bacteria from Membrane, to prevent Moisture Penetration", Derwent Publ. Ltd. FREN, Aug. 5, 1986.

Fujisawa, "Long-Acting Oral Prepn.—comprises Rapidly Soluble Inner Layer and Sustained Release Outer Layer, Both Layers Containing Principal Agent, which is Coronary or Peripheral Vasodilator", FUJI, Sep. 20, 1991.

Gallagher, et al., "The Effects of Traditional Antidiabetic Plants on In Vitro Glucose Diffusion", Nutrition Research, 23 (2003), pp. 413-424.

Gartrell, et al., "The Effects of Chocolate and Chocolate by-product Consumption on Wild and Domestic Animals", Chocolate in Health and Nutrition, Humana Press, 2013, pp. 135-141.

Gasche, et al., "IL-10 Secretion and Sensitivity in Normal Human Intestine and Infalmmatory Bowel Disease", Journal of Clinical Immunology, vol. 20, No. 5, 2000.

German, et al., "Glucose Sensing in Pancreatic Islet Beta Cells: The Key Role of Glucokinase and the Glycolytic Intermediates", Proc. Nat. Acad. Sci., 90, 1781-1785 (1993).

Gibson, et al., "Dietary Modulation of the Human Gut Microflora Using Probiotics", Journal of Nutrition, 1998, 80, suppl 2, S209-S212.

Gielkens, et al., "Effects of Hyperglycemia and Hyperinsulinemia on Satiety in Humans", Metabolism, vol. 47, No. 3, pp. 321-324, 1998.

Goldrosen, et al., "Impaired Lymphocyte Blastogenic Response in Patients with Colon Adenocarcinoma: Effects of Disease and Age", Journal of Surgical Oncology, 9:229-234, 1977.

Golkar, et al., "Apigenin Inhibits Pancreatic Cancel Cell Proliferation via Down-Regulation of the GLUT-1 Glucose Transporter", Gastroenterology, vol. 130, No. 4, Jul. 22, 2006.

Gondwe, "Effects of Persea Americana Mill (Lauraceae) Ethanolic Leaf Extract on Blood Glucose and Kidney Function in Streptozotocin-Induced Diabetic Rats and on Kidney Cell Lines of the Proximal (LLC-PK1) and Distal Tubules (MDBK)", Methods Find Exp Clin. Pharmacol., 2008, 30(1), pp. 25-35.

Grajales-Lagunes, et al., "Stability and Sensory Quality of Spray Dried Avocado Paste", Drying Technology, Vo. 17, No. 1&2, 1999, pp. 317-326.

Greetham, et al., "Bacteriology of the labrador dog gut: A cultural and genotype approach", J. Appl. Microbiol., 93:640-646, 2002.

Groux, et al., "Regulatory T Cells and Inflammatory Bowel Disease", Viewpoint Immunology Today, Oct. 1999.

Guo, et al., "In Vivo 2-Deoxyglucose Administration Preserves Glucose and Glutamate Trasport and Mitochondrial Function in Cortical Synaptic Terminals after Exposure to Amyloid Beta-Peptide and Iron: Evidence for a Stress Response", Experimental Neurology, vol. 166., No. 1, Jan. 1, 2000, XP008056810, pp. 173-179.

Hammarstrom, et al., "Mitogenic Leukoagglutinin from Phaseolus vulgaris Binds to a Pentasaccharide Unit in N-acetyllactosamine-type Glycoprotein Glycans", Proc. Natl. Acad. Sci. USA, 79, 1611-1615 (1982).

Hemme, et al., "Lactobacillus murinus JCM1717", Database JCM Catalogue, Japan Collection of Microorganisms, 1982, XP002447036.

Henrotin, et al., "Pharmaceutical and Nutraceutical Management of Canine Osteoarthritis: Present and Future Perspectives", The Veterinary Journal, 170 (2005), pp. 113-123.

Hershkovitz, et al., "Ethylene regulation of Avocado Ripening Differs Between Seeded and Seedless Fruit", Postharvest Biology and Technology, vol. 56, No. 2, May 1, 2010, pp. 138-146.

Hildesheim, et al., "Simultaneous Measurement of Several Cytokines Using Small Volumes of Biospecimens", Cancer Epidemiology, Biomarkers & Prevention, vol. IK1, pp. 1477-1484, Nov. 2002, abstract.

Hillsvet, "Hill's Presciption Diet, A New Way to Define Pet Obesity", Internet Article, http://www.hillsvet.com/conference-documents/Weight_Management/Therapeutic?Weight_Reduction_Program/BFI_Backgrounder.pdf.

Hoffman, et al., "Diabetogenic Action of 5-Thio-D-glucopyranose in Rats", Biochemistry, vol. 7, pp. 4479-4483 (1968).

Hommes, et al., "Anti- and Proinflammatory Cytokines in the Pathogenesis of Tissue Damage in Crohn's Disease", 2000 Lippincott Williams and Wilkins, pp. 1363-1950.

Isolauri, et al., "Probiotics: A Role in the Treatment of Intestinal Infection and Inflammation?", Gut, 2002, 50 (Suppl III), pp. iii54-iii59.

Issekutz, et al., "Effect of Mannoheptulose on Glucose Kinetics in Normal and Glucocorticoid Treated Dogs", Life Sciences, 15(4), pp. 635-643, 1974.

Iwasaki, et al., "Unique Functions of CD11b+, CD8a+ and Double Negative Peyer's Patch Dendritic Cells", 2001, The American Association of Immunologists.

Jay, et al., "Metabolic Stability of 3-O-Methyl-D-Glucose in Brain and Other Tissues", J. Neurochem., 55, pp. 989-1000 (1990).

Johnson, et al., "Glucose-Dependent Modulation in Insulin Secretion and Intracellular Calcium Ions by GKA50, a Glucokinase Activator", Diabetes, vol. 56, Jun. 2007, pp. 1694-1702.

All Office Actions, U.S. Appl. No. 09/950,052.
All Office Actions, U.S. Appl. No. 10/842,300.
All Office Actions, U.S. Appl. No. 11/313,198.
All Office Actions, U.S. Appl. No. 11/313,199.
All Office Actions, U.S. Appl. No. 12/012,317.
All Office Actions, U.S. Appl. No. 12/082,710.
All Office Actions, U.S. Appl. No. 12/168,400.
All Office Actions, U.S. Appl. No. 12/371,101.
All Office Actions, U.S. Appl. No. 12/371,266.
All Office Actions, U.S. Appl. No. 12/638,128.
All Office Actions, U.S. Appl. No. 12/716,533.
All Office Actions, U.S. Appl. No. 12/762,539.
All Office Actions, U.S. Appl. No. 12/939,594.
All Office Actions, U.S. Appl. No. 13/098,741.
All Office Actions, U.S. Appl. No. 13/098,756.
All Office Actions, U.S. Appl. No. 14/043,142.

Amendment in response to Nonfinal Office Action dated Aug. 16, 2011 and issued in connection with U.S. Appl. No. 12/716,540 dated Nov. 15, 2011.

Amendment in response to Nonfinal Office Action dated Jun. 10, 2011 and issued in connection with U.S. Appl. No. 12/638,101, dated Sep. 2, 2011.

Amendment in response to Nonfinal Office Action dated Jun. 7, 2011 and issued in connection with U.S. Appl. No. 12/716,518 dated Oct. 7, 2011.

Amendment in response to Nonfinal office Action dated Jun. 9, 2011 and issued in connection with U.S. Appl. No. 12/716,562, dated Sep. 2, 2011.

Archived pages from HTTP://web.archive.org for http://medtechnologies.com dated Feb. 2003.

Blue Buffalo Life Protection Formula_package.pdf, http//www.bluebuff.com/products/dogs/lp-adult-chick.shtml Information accessed Feb. 3, 2009.

(56) References Cited

OTHER PUBLICATIONS

Breeders Choice, AvoDERM product brochures http://www.breeders-choice.com/about/brochures.htm, Information accessed Feb. 3, 2009.
Dorland's Pocket Medical Dictionary (24th ed.), W.B. Saunders Co. p. 15, 1989.
European Search Report Received in Connection with EP 04 81 5182, dated Jun. 13, 2008.
European Search Report Received in Connection with EP 04 81 5186, dated Jan. 7, 2013.
Final Office Action issued in connection with U.S. Appl. No. 12/638,101, dated Dec. 30, 2011.
Final Office Action issued in connection with U.S. Appl. No. 12/716,518 dated Jan. 4, 2012.
Final Office Action issued in connection with U.S. Appl. No. 12/716,540 dated Jan. 10, 2012.
Final Office Action issued in connection with U.S. Appl. No. 12/716,562 dated Dec. 29, 2011.
International Search Report for PCT/US2011/058861, dated Feb. 10, 2012.
International Search Report for PCT/US2012/035921, dated Jul. 10, 2012.
International Search Report for PCT/US2012/036035, dated Jul. 11, 2012.
International Search Report Received in Connection with PCT/IB2008/050382, dated Oct. 7, 2008.
International Search Report Received in Connection with PCT/US2004/043068, dated Sep. 25, 2007.
Natures Logic Natural Chicken Dinner Fare FROZEN_package.pdf http://www.natureslogic.com/products/dp_rf_chi.html, Information accessed Feb. 3, 2009.
Natures Logic Natural Chicken Meal_package.pdf http://www.natureslogic.com/products/dp_dry_chi.html, Information accessed Feb. 3, 2009.
Nonfinal Office Action issued in connection with U.S. Appl. No. 12/638,101, dated Jun. 10, 2011.
Nonfinal Office Action issued in connection with U.S. Appl. No. 12/716,540, dated Aug. 16, 2011.
Nonfinal Office Action issued in connection with U.S. Appl. No. 12/716,562, dated Jun. 9, 2011.
Nonfinal Office Action issued in connection with U.S. Appl. No. 12/716,518 dated Jun. 7, 2011.
Physician's Desk Reference, 1963 Edition, Medical Economics, Inc. Oradell, N.J., 1962, Product Identification Section, SEction Four, p. VIII and XI.
Publication downloaded from http://en.wikipedia.org/wiki/Noni on May 4, 2009, 9 pages.
Supplemental Amendment in response to Nonfinal Office Action dated Jun. 10, 201, and issued in connection with U.S. Appl. No. 12/638,101, dated Sep. 29, 2011.
LabScan XE User's Manual, Manual Version 1.2, A60-1010-862, Jan. 2003, 53 pages.
"A Balanced Diet", Waltham Book of Dog and Cat Nutrition, Ed. ATB, Edney, Chapter by A. Rainbird, pp. 57-74, Pergamon Press, Oxford.
"Changing Times", The Kiplinger Magazine, vol. 31, No. 1, Jan. 1977, pp. 39-40.
"Kidney Stones in Adults (http://kidney.niddk.nih.gov, pp. 1-14)."
"Lactobacillus animalis genes for 16S-23S intergenic spacer region, 23S ribosomal RNA, strain", DATABASE EMBL: JCM 5670, Jul. 9, 2004, XP002447038.
"Lactobacillus murinus genes for 16S-23S intergenic spacer regions, 23S ribosomal RNA, strain: JCM 1717", Database EMBL, Jul. 9, 2004, XP002447039.
Seikagaku jiten (third edition), Tokyo Kagaku Dojin Publishing Co., Inc., 1998, pp. 657-658.
"Mice and Rats", (www.petswarehouse.com, pp. 1-5).
"Nutrient Profiles for Dog Foods", Association of American Feed Control Officials Incorporated, pp. 110-119, 1994.
"Probiotic Basics", (www.usprobiotics.org.basics/, p. 1-12).
"Urinary Tract Infections in Adults", (http://kidney.niddk.nih.gov, pp. 1-11).
Adeyemi, et al., "Analgesic and Anti-Inflammatory Effects of the Aqueous Extract Leaves of Persea America Mill (Lauraceae)", Fitoterapia, IDB Holdings, Milan, IT, vol. 73, No. 5, Aug. 1, 2002, pp. 375-380, XP002318086.
Alves-Filho, Drying Technology, 2002, vol. 20, No. 8, pp. 1541-1557, abstract.
Anand, et al., "Cytokines and Inflammatory Bowel Disease", Tropical Gastroenterology, 1999, 20(3), pp. 97-106.
Anderson, et al., Nutrition Reviews, vol. 61, No. 5, pp. S17-S26, May 2003.
Andus, et al., "Imbalance of the Interleukin 1 System in Colonic Mucosa—Association with Intestinal Inflammation and Interleukin 1 Receptor Agonist Genotype 2", Gut, vol. 31, 1997, pp. 651-657.
Anonymous, "The Best Ever Guacamole—Again, Whole Foods Market", Jan. 18, 2013, Retrieved from the Internet: URL:http://www.wholefoodsmarket.com/blog/best-ever-guacamole-again, p. 3.
Apgar, et al., "Effect of feeding Various Levels of Bifidobacterium globosum A on the Performance, Gastrointestinal Measurements and Immunity of Weanling Pigs and on the Performance and Carcass Measurements of Gorwing-Finishing Pigs", J. Animal Science, 1993, Vo. 71, pp. 2173-2179.
Appelboom, et al., "Symptoms Modifying Effect of Avocoda/Soybean Unsaponfiables (ASU) in Knee Arthritis. A Double Blind, Prospective, Placebo-Controlled Study", Scandinavian Journal of Rheumatology, vol. 30, pp. 242-247 (2001).
Arai, et al., "Cytokines: Coordinates of Immune and Inflammatory Responses", Annu. Rev. Biochem., 90, 59: 783-836.
Aranda, et al., "Analysis of Intestinal Lymphocytes in Mouse Colitis Medicated by Transfer of CD4+, CD45RB High T Cells in SCID Recipients", 1997, The American Assoc. of Immunologists.
Arany, et al., "The Effect of Carcinogens and Non-Carcinogens on Some Biochemical Features of the Mouse Lung Tissue", Arch. Toxicol., Suppl. 4, 73 (1980).
Asahara, et al., "Antimicrobial Activity of Intraurethrally Adminstered Probiotic Lactobacillus casei in a Murine Model of *Escherichia coli* Urinary Tract Infection", Antimicrobial Agents & Chemotherapy, 2001, 45(6): 1751-1760.
Ashcroft, et al., "Glucose Metabolism in Mouse Pancreatic Islets", Biochem. J. (1970), 118, pp. 143-154.
Au, et al., "Avocado Soybean Unsaponifiables (ASU) suppress TNF-a, IL-1b, cox-2, iNOS Gene Expression, and Prostaglandin E2 and Nitric Oxide Production in Articular Chondrocytes and Monocyte/Macrophages", Osteoarthritis and Cartilage, 2007, 15, 18 pages.
Balkau, et al., "Insulin resistance: an independent risk factor for cardiovascular disease?", Diabetes Obes. Metab., 1 (Suppl. 1), pp. S23-S31, 1999.
Barbara, et al., "A Role for Inflammation in Irritable Bowel Syndrome", Gut, 2002, 51 (Suppl I), pp. i41-i44.
Barge, "Avocados May Help Prevent Oral Cancer, OSU Study Shows", Journal of Dental Hygiene, vol. 82, No. 2, Apr. 2008, 3 pp.
Barrows, et al., "Diet and Nutrition", Walleye Culture Manual, R. C. Summerfelt, editor, NCRAC Culture Series 101, North Central Regional Aquaculture Center Publications Office, Iowa State University, Ames.
Begbie, et al., "The Isolation of Some Heptoses, Heptuloses, Octuloses and Nonuloses from Pimula Officinalis JACQ", Carbohydrate Research, 1966, vol. 2, pp. 272-288.
Benno, et al., "Individual and Seasonal Variations in the Composition of Fecal Microflora of Beagle Dogs", Bifidobacteria Microflora, vol. 11, No. 2, pp. 69-76, 1992.
Biavati, et al., "Electrophoretic Patterns of Proteins in the Genus *Bifidobacterium* and Proposal of Four New Species", Journal Int. J. Syst. Bacteriol., vol. 32, pp. 358-373, 1982.
Blatherwick, et al., "Metabolism of D-Mannoheptulose. Excretion of the Sugar After Eating Avocado", J. Biol. Chem., vol. 133, pp. 643-650 1940.
Board, et al., "High KM Glucose Phosphorylating (Glucokinase) Activities in a Range of Tumor Cell Lines and Inhibition of Rates

(56) References Cited

OTHER PUBLICATIONS of Tumor Growth by the Specific Enzyme Inhibitor Mannoheptulose", Cancer Research, vol. 55, pp. 3278-3285, Aug. 1995.
Bodmeier, "Capsule with Controlled Active Ingredient Release Comprises Active Ingredient Containing Filling, Capsule Shell, Swelling Agent and Water-Insoluble Layer", BODM, May 18, 1999.
Botterweck, et al., "Intake of Butylated Hydroxyanisole and Butylated Hydroxytoluene and Stomach Cancer Risk: Results from Analyses in the Netherlands Cohort Study", Food and Chemical Toxicology, 38 (2000, 599-605.
Bouhnik, et al., "Effects of Bifidobacterium SP Fermented Milk Ingested with or without Inulin on Colonic Bifidobacteria and Enzymatic Activities in Healthy Humans", European Journal of Clinical Nutrition, 1996, 50, pp. 269-273.
Brai, et al., "Hypoglycemic and Hypocholesterolemic Potential of Persea Americana Leaf Extracts", J. Med. Food, 2007, pp. 356-360.
Brandtzaeg, et al., "Immunopathology of Human Inflammatory Bowel Disease", Springer Seminars in Immunopathology, 1997, 18, pp. 555-589.
Bredif, et al., "Avocado Sugars are Effective Inducer of Cutaneous Defensive Functions", Journal of the American Academy of Dermatology, St. Loius, Mo, vol. 50, No. 2, Feb. 1, 2007, p. AB84, XP005937005.
Bridigidi, et al., "Specific Detection of Bifidobacterium Strains in a Pharmaceutical Probiotic Product and in Human Feces by Polymerase Chain Reaction", System Appl. Microbiol., 23, 2000, 391-399.
Brown, et al., "Glucose Phosphorylation is Essential for the Turnover of Neutral Lipid and the Second Stage Assembly of Triacylglycerol-Rich ApoB-Containing Lipoproteins in Primary Hepatocyte Cultures", American Heart Association, Inc., 1999, pp. 321-329.
Burger, et al., "Cardiomyopathy in Ostriches (*Struthio camelus*) Due to Avocado (*Persea americana* Var. *guatemalensis*) Intoxication", Journal of the South African Veterinary Association, vol. Jaargang 65, No. 2, Jun. 1994.
Campieri, et al., "Reduction of Oxaluria after an Oral Course of Lactic Acid bacteria at High Concentration", Kidney International (2001) vol. 60, pp. 1097-1105.
Carranza, et al., "Lower Quantities of Avocado as Daily Source of Monounsaturated Fats: Effect on Serum and Membrane Lipids, Endothelial Function, Platelet Aggregation and C-Reactive Protein in Patients with Metabolic Syndrome", Database Embase, Elsevier Science Publishers, Amsterdam NL, Nov. 2004, XP002485347.
Chadwick, et al., "Activation of the Mucosal Immune System in Irritable Bowel Syndrome", Gastroenterology, 2002, 122, pp. 1778-1783.
Chan, et al., "Ultra Structural and Secretory Heterogeneity of fa/fa (Zucker) Rat Islets", Molecular and Cellular Endocrinology, 136, 1998, pp. 119-129.
Charteris, et al., "Antibiotic Susceptibility of Potentially Probiotic Bifidobacterium Isolates from the Human Gastrointestinal Tract", Letters in Applied Microbiology, 1998, vol. 26, pp. 333-337.
Charteris, et al., "Development and Application of an In Vitro Methodology to Determine the Transit Tolerance of Potentially Probiotic *Lactobacillus* and *Bifidobacterium* Species in the Upper Human Gastrointestinal Tract", Journal of Applied Microbiology, 1998, vol. 84, pp. 759-768.
Chateris, et al., "Effect of Conjugated Bile Salts on Antibiotic Susceptibility of Bile Salt-Tolerant Lactobacillus and Bifidobacterium Isolates", Journal of Food Protection, vol. 63, No. 10, 2000, pp. 1369-1376.
Charteris, et al., "Selective Detection, Enumeration and Identification of Potentially Probiotic *Lactobacillus* and *Bifidobacterium* Species in Mixed Bacterial Populations", International Journal of Food Microbiology, 35, 1997, pp. 1-27.
Chauviere, et al., "Adhesion of Human Lactobacillus Acidophilus Strain LB to Human Enterocyte-like Caco-2 Cells", Journal of General Microbiology, 1992, vol. 138, pp. 1689-1696.

Chen, et al., "Action of 5-Thio-D-Glucose and Its 1-Phosphate with Hexokinase and Phosphoglucomutase", Arch. Biochem. Biophys. 169, pp. 392-396 (1975).
Chevalier, et al., "Detection of *Bifidobacterium* Species by Enzymatic Methods", Journal of Applied Bacteriology, 1990, vol. 68, pp. 619-624.
Chiricolo, et al., "Cell Adhesion Molecules CD11a and CD18 in Blood Monocytes in Old Age and the Consequences for Immunological Dysfunction", Gerontology, 1995, 41(4), pp. 227-234.
Cicco, et al., "Inducible Production of Interleukin-6 by Human Polymorphonuclear Neutrophils: Role of Granulocyte-Macrophage Colony-Stimulating Factor and Tumor Necrosis Factor-Alpha", The American Society of Hematology, Blood, vol. 75, No. 10, May 15, 1990, pp. 2049-2052.
Collins, et al., "A Randomised Controlled Trial of a Probiotic Lactobacillus Strain in Healthy Adults: Assessment of its Delivery, Transit and Influence on Microbial Flora and Enteric Immunity", Microbial Ecology in Health and Disease, vol. 14, No. 2, Jun. 2002, pp. 81-89.
Miller, et al., "The Metabolic Stressor 2-Deoxy-D-Glucose (2-DG) Enhances LPS-Stimulated Cytokine Production in Mice", Brain, Behavior, and Immunity, 1993, vol. 7, pp. 317-325, 1993, 317-325.
Mitsuoka, et al., "Ecology of the Bifidobacteria.", The American Journal of Clinical Nutrition, Nov. 1977, vol. 30, pp. 1799-1810.
Mohamed, et al., "Effect of Long-Term Ovariectomy and Estrogen Replacement on the Expression of Estrogen Receptor Gene in Female Rats", Eur. J. Endocrinol., 15, 142:307-14, 2000.
Monteleone, et al., "Manipulation of Cytokines in the Management of Patients with Inflammatory Bowel Disease", Ann. Med, Nov. 2000, 32(8), pp. 552-560.
Morishita Jintan KK, "Capsule Preparation for Enteral Adminstration of Unsaturated Fatty Acids", Derwent Publications Ltd, MORI, Oct. 30, 1997.
Morishita Jintan KK, "Yogurt for Supply Physiologically Important Intestinal Bacteria—Contains Bacteria Contained in Capsule Havingn Inner Layer Made of Digestible Substance and Outer Layer Dissolving in Intesting", MORI.
Moustafa, et al., "Effects of aging and antioxidants on glucose transport in rat adipocytes", Gerontology, 1995, 41(6):301-7.
Murphy, et al., "Evaluation and Characterisation of Probiotic Therapy in the CD45RB Transfer Model of Colitis", AGA Abstracts, Gastroenterology, vol. 116, No. 4.
Naaz, et al., "THe Soy Isoflavone Genistein Decreases Adipose Deposition in Mice", Endocrinology, 144(8):3315-3320, 2003.
Naveh, et al., "Detailed Avocado Pulp Reduces Body Weight and Total Hepatic Fat but Increases Plasma Chloesterol in Male Rats fed Diets with Cholesterol", Am. Soc. for Nutritional Sciences, 2002, 2015-2018.
Nordal, et al., "Isolation of Mannoheptulose and Identification of its Phosphate in Avocado Leaves", J. Am. Chem. Soc., 1954, vol. 76, No. 20, pp. 5054-5055.
Nordal, et al., "Isolation of Mannoheptulose and Identification of its Phosphate in Avocado Leaves", Meddelelser fra Norsk Farmaceutisk Selskap, (1955), 17, 207-213.
Novogrodsky, et al., "Lymphocyte Transformation Induced by Concanavalin A and its Reversion by methyl-alpha-D-mannopyranoside", Biochim. Biophys. Acta, 1971, 228, 579-583.
Obaldiston, et al., "Microflora of Alimentary Tract of Cats", American Journal of Veterinary Research, vol. 32, No. 9, Sep. 1971, pp. 1399-1405.
O'Callaghan, et al., "Differential Cytokine Response of Cells Derived from Different Lymphoid Compartments to Commensal and Pathogenic Bacteria", Gastroenterology, Apr. 2003, vol. 124, Issue 4, Supplement 1, p. A339.
O'Callaghan, et al., "Human Cytokine Production by Mesenteric Lymph Node Cells in Response to Probiotic and Pathogenic Bacteria", Gastroenterology, vol. 111, No. 4, Suppl. 1., pp. A389-S390 DDW Meeting Abstract No. T962, XP09036733.
Ogawa, Journal of Japan Mibyou System Association, 2004, vol. 10, No. 1, p. 140-142 (with machine translation), 2004, 140-142.
O'Halloran, et al., "Adhesion of Potential Probiotic Bacteria to Human Epithelial Cell Lines", Departments of Microbiology and

(56) References Cited

OTHER PUBLICATIONS

Medicine, University College, Mercy Hospital, Cork, Ireland, Dept of Surgery, Mercy Hospital Cork, Ireland.
Ojewole, et al., "Cardiovascular Effects of Persea Americana Mill (Lauraceae)(avocado) aqueous Leaf Extract in Experimental Animals", Cardiovasc. J. Afr., 2007, 18, pp. 69-76.
O'Mahony, et al., "Probiotic Bacteria and Pathogenic Bacteria Elicit Differential Cytokine Responses from Dendritic Cells", XP-001097379.
O'Mahony, et al., "Probiotic Bacteria and the Human Immune System", Dept Microbiology and Medicine, National Food Biotechnology Centre, University College, Cork & Dept Surger, Mercy Hospital Cork, Ireland.
O'Mahony, et al., "Probiotic Human Bifidobacteria: Selection of a New Strain and Evaluation in Vitro and In Vivo", Gastroenterology, vol. 118, No. 4, Apr. 2000.
O'Mahony, et al., "Probiotic Impact on Microbial Flora, Inflammation and Tumour Development in IL-10 Knockout mice", Aliment Pharmacol Ther., 2001, 15, pp. 1219-1225.
Panwala, et al., "A Novel Model of Inflammatory Bowel Disease: Mice Deficient for the Multiple Drug Resistance Gene, mdria, Spontaneously Develop Colitis", The American Association of Immunologists, 1998, The Journal of Immunology, 1998, 161, pp. 5733-5744.
Park, et al., "Species Specific Oligonucleotide probes for the detection and identification of Lactobacillus isolated from mouse feces", Journal of Applied Microbiology, 2005, vol. 99, pp. 51-57, XP002447051.
Pawelec, et al., "T Cell Immunosenescence In Vitro and In Vivo", Exp. Gerontol, 1999, 34: 419-429.
Pelicano, et al., "Glycolysis Inhibition for Anticancer Treatment", Oncogene, 2006, 25, pp. 4633-4646.
Perlmann, et al., "Inhibition of Cytotoxicity of Lymphocytes by Concanavalin A in vitro", Science, 1970, 168:1112-1115.
Poehlman, et al., "Caloric Restriction Mimetics: Physical Activity and Body Composition Changes", Journal of Gerontology, Series A 2001, vol. 56A (Special Issue I):45-54.
Powrie, et al., "Inhibition of Th1 Responses Prevents Inflammatory Bowel Disease in Scid Mice Reconstituted with CD45Rbhi CD4+ T Cells", Immunity, vol. 1, pp. 553-562, Oct. 1994.
Purina, "Advancing Life Through Diet Restriction", The Purina Pet Institute Symposium, 2002.
Ramsey, et al., "Dietary Restriction and Aging in Rehesus Monkeys: The University of Wisconsin Study", Experimental Gerontology, 35 (2000) 1131-1149.
Raonimalala, et al., "Action of Soluble Carbohydrates from Avocado Fruit on Utilization of Calcium in the Rat", Ann. Nutr Aliment, 34(4), 734-744, 1980.
Rastall, "Baceria in the Gut: Friends and Foes and How to Alter the Balance", The Journal of Nutrition, Waltham Intl Science Symposium: Nature, Nurture, and the Case for Nutrition (2004), pp. 2022S-2026S.
Reid, et al., "Prevention of Urinary Tract Infection in Rats with an Indigenous Lactobacillus Casei Strain", Infection and Immunity, 1985, 49(2), pp. 320-324.
Rezek, et al., "Glucose Antimetabolites and Hunger", J. Nutr., 106:143-157 (1976).
Rezek, et al., "Insulin Dependence of Paradoxical Overeating: Effect of Mannoheptulose, Somatostatin, and Cycloheximide", The American Physiological Society, 1979, E205-E211.
Ridker, et al., "C-Reactive Protein, the Metabolic Syndrome and Risk of Incident Cardiovascular Events: An 8-Year Follow-up of 14,719 Initially Healthy American Women", Circulation, vol. 107, No. 3, pp. 391-397.
Riquelme, et al., "Regulation of Carbohydrate Metabolism by 2,5-Anhydro-D-Mannitol", PNAS, 80, pp. 4301-4305 (1983).
Robey, et al., "Akt, Hexokinase, mTOR: Targeting Cellular Energy Metabloism for Cancer Therapy", Drug Discovery Today: Disease Mechanisms, vol. 2, No. 2, 2005, pp. 239-246.
Rodtong, et al., NCBI Genbank Accession No. AF080100, NCBI Genbank (1998).
Roe, et al., "Further Studies of the Physiological Availability of Heptoses", J. Biol. Chem., 121:37-43, 1937.
Roe, et al., "The Utilization of D-Mannoheptulose by Adult Rabbits", J. of Biological Chemistry, 112, 443-449, Jan. 1, 1936.
Rogler, et al., "Cytokines in Inflammatory Bowel Disease", World Journal of Surgery, vol. 22, 1998, pp. 382-389 XP002296948.
Roth, et al., "Caloric Restriction in Primates and Relevance to Humans", Ann. NY Acad. Aci., 928: 305-315, 2001.
Rowland, et al., "Physiological and Behavioral Responses to Glucoprivation in the Golden Hamster", Physiology and Behavior, vol. 30, No. 5, May 1, 1983, pp. 747-747.
Ruscetti, et al., "Release of Colony-Stimulating Activity from Thymus-Derived Lymphocytes", J Clin Invest. 1975;55(3):520-527.
Sakata, et al., "Feeding Modulation by Pentose and Hexose Analogues", Am. J. Clin. Nutr., 1992, 55:272-277S.
Sayegh, et al., "Impact of Hormone Replacement Therapy on the Body Mass and Fat Compositions of Menopausal Women: A Cross-Sectional Study", Menopause, 6:312-315, 1999.
Scarbrough, et al., "2-Deoxy-D-Glucose and 17-(allylaminio)-17-demethoxygeldanamycin Enhances Toxicity as wella s Increases Parameters Indicative of Oxidative Stress", Free Radical Biology and Medicine, vol. 43, suppl. 1, Nov. 14, 2007, p. S59.
Yu, "Aging and Oxidative Stress: Modulation by Dietary Restriction", Free Radical Biology and Medicine, vol. 21, No. 5, pp. 651-668, 1996.
Yu, et al., "Modulation of Aging Processes by Dietary Restriction", CRC Press, Boca Raton (1994).
Zhang, et al., "Dissimilar Effects of D-Mannoheptulose on the phosphorylation of alpha vs beta-D-glucose by either Hexokinase or Glucokinase", International Journal of Molecular Medicine, 14, pp. 107-112, 2004.

* cited by examiner

SEQUENCE LISTING

<160> NUMBER OF SEQ ID NOS: 4

<210> SEQ ID NO 1
<211> LENGTH: 556
<212> TYPE: DNA
<213> ORGANISM: Bifidobacteria globosum
<220> FEATURE:
<221> NAME/KEY: misc_feature
<222> LOCATION: (460)..(460)
<223> OTHER INFORMATION: n is c, g, a or t.
<220> FEATURE:
<221> NAME/KEY: misc_feature
<222> LOCATION: (549)..(549)
<223> OTHER INFORMATION: n is c, g, a or t.

<400> SEQUENCE: 1
acgatttgtg ggcgcacggt ggtgcgccga tatgggatg cttccttttc ctggccgtct      60
ggccgggtgg cgtcccttgc tggctgggaa aagggtcaag gcgcctgcgc ccgttgtggt     120
gtgggtggtg gtggtgtggt gcatgctgtt gggttcccgg accgccaggc cccttgtcgg    180
gggtggtgtt ccgttcccgc cgtcctgccc gtgcccctgt gtggggtggg tgcctggggt    240
ggtgtggtgt ggtggtttga gaactggaga gtggacgcga gcatgaacgg tgtgccctgt    300

```
ggggtgtgcc gggtgtgttc gtactgttga ttttgtcgaa ccgttccatc cccgccttt    360 gggttggggg tgttggattg tgttcgcgag tgttttggta gagccgtcca cgcccgtgtg    420
ggtgtgggtg gtgtttagat gatctgatta gttgtcgtan ggtgttccag tgcaagtggc    480
atgggcccgt ggccccctt tgcggggttg gtgggtttgt tgccatgggc gtatggtgga    540
atgcctgtnc accacg                                                    556

<210> SEQ ID NO 2
<211> LENGTH: 526
<212> TYPE: DNA
<213> ORGANISM: Bifidobacterium pseudolongum
<220> FEATURE:
<221> NAME/KEY: misc_feature
<222> LOCATION: (494)..(494)
<223> OTHER INFORMATION: n is a, t, g or c
<220> FEATURE:
<221> NAME/KEY: misc_feature
<222> LOCATION: (510)..(510)
<223> OTHER INFORMATION: n is a, t, g or c
<220> FEATURE:
<221> NAME/KEY: misc_feature
<222> LOCATION: (518)..(518)
<223> OTHER INFORMATION: n is a, t, g or c

<400> SEQUENCE: 2
tggggcacgg tagtgcccga tatgggatgc ttcctttcct ggccgtgtgg ccgggtggtg     60
tcccttgctg gctggaaaaa ggtcaaggcg cctgcgccct tgtggtgtgg gtggacagtg    120
gtgtggtgca tgctgttggg ttcccggacc gccaggcccc ttgtcggggg tggtgttccg    180
ttcccgccgt cctggccgtg ccccttgtgg ggtgggtgcc tggggtggtg tggtgtggtg    240
gtttgagaac tggagagtgg acgcgagcat gaacggtgtg ccttttgggg tgtgccgggt    300
gtgttcgtac tgttgatttt gtcgaaccgt tccgtgcccg cctttcgggt gggtgcgtgg    360
attgtgttcg cgagtgtttt ggtaagcccc ccgcactgtt ggtgtgggtg gtgtttaaat    420
gatctgatta attgtcgtaa ggtgttccag tgcaagtggc atgggcccgt ggccccctt    480 ttgcggggt tggngggttt tttccatggn cgtatggngg aatcct                   526

<210> SEQ ID NO 3
<211> LENGTH: 18
<212> TYPE: DNA
<213> ORGANISM: Artificial
<220> FEATURE:
<223> OTHER INFORMATION: Chemically synthesized nucleotide sequence

<400> SEQUENCE: 3
gctggatcac ctcctttc                                                   18

<210> SEQ ID NO 4
<211> LENGTH: 18
<212> TYPE: DNA
<213> ORGANISM: Artificial
<220> FEATURE:
<223> OTHER INFORMATION: Chemically synthesized nucleotide sequence

<400> SEQUENCE: 4
ctggtgccaa ggcatcca                                                   18
```

METHODS OF USE OF PROBIOTIC BIFIDOBACTERIA FOR COMPANION ANIMALS

CROSS REFERENCE TO RELATED APPLICATION

This Application claims the benefit of U.S. Provisional Application No. 60/531,597 filed on Dec. 19, 2003.

FIELD OF THE INVENTION

The present invention relates to the field of probiotic *Bifidobacteria*, more specifically methods of use of probiotic *Bifidobacteria* in companion animals.

BACKGROUND OF THE INVENTION

The defense mechanisms to protect the mammalian gastrointestinal (GI) tract from colonisation by bacteria are highly complex. The GI tract of most mammals are colonised by native microflora, and invasive pathogenic microorganisms. In a healthy state, these competing microflora are in a state of equilibrium. Modification of the intestinal microflora equilibrium may lead to or prevent many GI disorders, both in humans, and other mammalian species, such as companion animals including cats, dogs and rabbits. The well being of companion animals is closely related to their feeding and GI health, and maintenance of the intestinal microflora equilibrium in these animals may result in healthier pets.

The number and composition of the intestinal microflora tend to be stable, although age and diet may modify it. Gastric acidity, bile, intestinal peristaltic and local immunity are factors thought to be important in the regulation of bacterial flora in the small intestine of human beings and various other mammals. Often pet GI disorders, including those found in canines and felines, are linked to bacterial overgrowth and the production of enterotoxins by pathogenic bacteria. These factors disrupt the intestinal microflora equilibrium and can promote inflammation and aberrant immune responses.

Recently, research has begun to highlight some valuable strains of bacteria obtainable by isolation from resected and washed gastrointestinal tract of mammals, such as humans and canines, and their potential use as probiotic agents. Probiotics are considered to be preparations of bacteria, either viable or dead, their constituents such as proteins or carbohydrates, or purified fractions of bacterial ferments that promote mammalian health by preserving the natural microflora in the GI tract, and reinforcing the normal controls on aberrant immune responses. It is believed by some that probiotic bacteria are more effective when derived from the species, or closely related species, intended to be treated. Whilst several strains of probiotic bacteria have been elucidated, methods of use of these strains and their therapeutic efficacy has been limited to modulation of gastro-intestinal disorders in humans. As yet, there has not been much investigation into the potential for these organisms to beneficially affect physiological systems other than the gastro-intestinal tract in companion animals, such as canines and felines.

SUMMARY OF THE INVENTION

According to the present invention, there is provided methods of use of probiotic *Bifidobacteria* obtainable by isolation from resected and washed gastrointestinal tract of mammals in companion animals. Said methods include treatment, either prophylactic or therapeutic, of the immune system, weight control and body composition, urinary health, skin and coat diseases, and aging.

These and other features, aspects and advantages of the present invention will become evident to those skilled in the art from reading the present disclosure.

DETAILED DESCRIPTION OF THE INVENTION

Sequences

SEQ. ID NO. 1-16s-23s intergenic spacer nucleotide sequence from *Bifidobacteria globosum* AHCF (NCIMB 41198).

SEQ. ID NO. 2-16s-23s intergenic spacer nucleotide sequence from *Bifidobacteria pseudolongum* AHC7 (NCIMB 41199).

SEQ. ID NO. 3-16s-23s left PCR primer sequences for sequence analysis.

SEQ. ID NO. 4-16s-23s right PCR primer sequences for sequence analysis.

Bacterial Deposit Numbers

The table below describes the species, strain number and deposit number for probiotic *Bifidobacteria* obtainable by isolation from resected and washed gastrointestinal tract of mammals useful in the present invention. The bacterial strains have been deposited with the National Collections of Industrial Food and Marine Bacteria (NCIMB), Aberdeen, UK.

| Strain Reference | NCIMB Deposit Number | Sequence Listing |
|---|---|---|
| AH208 | NCIMB 41050 | — |
| AH209 | NCIMB 41051 | — |
| AH210 | NCIMB 41052 | — |
| AH211 | NCIMB 41053 | — |
| AH212 | NCIMB 41099 | — |
| AH214 | NCIMB 41100 | — |
| AH35624 | NCIMB 41003 | — |
| AHC7 | NCIMB 41199 | SEQ. ID NO. 2 |
| AHCF | NCIMB 41198 | SEQ. ID NO. 1 |

All weights, measurements and concentrations herein are measured at 25° C. on the composition in its entirety, unless otherwise specified.

Unless otherwise indicated, all percentages of compositions referred to herein are weight percentages and all ratios are weight ratios.

Unless otherwise indicated, all molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

Within the following description, the abbreviation CFU ("colony-forming unit") designates the number of bacterial cells revealed by microbiological counts on agar plates, as will be commonly understood in the art.

As used herein, the term "mutants thereof" includes derived bacterial strains having at least 88% homology, preferably at least 90% homology, more preferably 95% homology to the 16s-23s intergenic spacer polynucleotide sequence of a referenced strain, but otherwise comprising DNA mutations in other DNA sequences in the bacterial genome.

As used herein, the term "DNA mutations" includes natural or induced mutations comprising at least single base alterations including deletions, insertions, transversions, and other DNA modifications known to those skilled in the art, including genetic modification introduced into a parent nucleotide or amino acid sequence whilst maintaining at least 50% homology to the parent sequence. Preferably, the sequence comprising the DNA mutation or mutations has at least 60%, more preferably at least 75%, more preferably still 85% homology with the parental sequence. As used herein, sequence "homology" can be determined using standard techniques known to those skilled in the art For example, homology may be determined using the on-line homology algorithm "BLAST" program, publicly available at http://www.ncbi.nlm.nih.gov/BLAST/.

As used herein "genetic modification" includes the introduction of exogenous and/or endogenous DNA sequences into the genome of an organism either by insertion into the genome of said organism or by vectors including plasmid DNA or bacteriophage as known by one skilled in the art, said DNA sequence being at least two deoxyribonucleic acid bases in length.

As used herein, "companion animal" means a domestic animal. Preferably, "companion animal" means a domestic canine, feline, rabbit, ferret, horse, cow, or the like. More preferably, "companion animal" means a domestic canine or feline.

The strain of lactic acid bacteria of the genus *Bifidobacteria globosum* obtainable by isolation from resected and washed canine gastrointestinal tract can be used to deliver probiotic benefit following oral consumption in animals, preferably companion animals or humans. This probiotic benefit generally maintains and improves the overall health of the animal. Non-limiting elements of animal health and physiology that benefit, either in therapeutically relieving the symptoms of, or disease prevention by prophylaxis include inflammatory disorders, immunodeficiency, inflammatory bowel disease, irritable bowel syndrome, cancer (particularly those of the gastrointestinal and immune systems), diarrhoeal disease, antibiotic associated diarrhoea, appendicitis, autoimmune disorders, multiple sclerosis, Alzheimer's disease, amyloidosis, rheumatoid arthritis, arthritis, joint mobility, diabetes mellitus, bacterial infections, viral infections, fungal infections, periodontal disease, urogenital disease, surgical associated trauma, surgical-induced metastatic disease, sepsis, weight loss, weight gain, excessive adipose tissue accumulation, anorexia, fever control, cachexia, wound healing, ulcers, gut barrier infection, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, and epidermal disorders. Preferred are treatment of the gastrointestinal tract, including treatment or prevention of diarrhoea; immune system regulation, preferably the treatment or prevention of autoimmune disease and inflammation; maintaining or improving the health of the skin and/or coat system, preferably treating or preventing atopic disease of the skin; ameliorating or reducing the effects of aging, including mental awareness and activity levels; and preventing weight loss during and following infection.

The treatment of the disorders disclosed above may be measured using techniques known to those skilled in the art. For example, inflammatory disorders including autoimmune disease and inflammation may be detected and monitored using in vivo immune function tests such as lymphocyte blastogenesis, natural killer cell activity, antibody response to vaccines, delayed-type hypersensitivity, and mixtures thereof. Such methods are briefly described herein, but well known to those skilled in the art.

1. Lymphocyte blastogenesis: This assay measures the proliferative response in vitro of lymphocytes isolated from fresh whole blood of test and control animals to various mitogens and is a measure of overall T- and B-cell function. Briefly, peripheral blood mononucleocytes (PBMC) are isolated from whole blood by Ficoll-Hypaque density centrifugation methods known to those skilled in the art. The isolated PBMCs are washed twice in RPMI 1640 cell media supplemented with HEPES, L-glutamine and penicillin/streptomycin. The washed cells are resuspended in RPMI 1640, counted, and the cell density adjusted appropriately. The $2\times10^5$ cells are exposed to a range of concentrations (0.1 □g/ml to 100 □g/ml) of various mitogens, some examples of which include pokeweed mitogen (Gibco), phytohaemagglutinin (Gibco) and conconavalin A (Sigma) in triplicate for 72 hours at 37° C. and 5% $CO_2$ with 10% foetal bovine serum (Sigma). At 54 hours the cells are pulsed with 1 □Ci $^3$H-thymidine, and the cells harvested and scintillation counts read on a TopCount NXT at 72 hours.

2. Natural killer cell activity: As described in U.S. Pat. No. 6,310,090, this assay measures the in vitro effector activity of natural killer cells isolated from fresh whole blood of test and control animals. Natural killer cells are a component of the innate immune function of a mammal. Canine thyroid adenocarcinoma cells were used as target cells in assessing NK cell cytotoxic activity. This cell line was previously shown to be susceptible to killing by canine NK cell. Target cells were cultured in a T75 flask with 20 mL minimum essential medium (MEM; Sigma Chem. Co., St. Louis, Mo.) supplemented with 10% fetal calf serum (FCS), 100 U/mL of penicillin and 100 .□g/mL of streptomycin. When confluent, target cells were trypsinized, washed 3 times and resuspended to $5\times10^5$ cells/mL in complete medium (RPMI-1640+10% FCS+100 U/mL of penicillin+100 □g/mL of streptomycin). Triplicate 100 .□L aliquots of the target cells were pipetted into 96-well U-bottom plates (Costar, Cambridge, Mass.) and incubated for 8 hours to allow cell adherence. Lymphocytes (effector cells; 100 .□L) isolated by Ficoll-Hypaque separation (as described above) were then added to the target cells to provide an effector/target cell (E:T) ratio of 10:1. After 10 hours of incubation at 37° C., 20 .□l of a substrate containing 5 .□g of 3-(4,5-dimethylthiazol-2-yl)-2,5-diphenyltetrazolium bromide (MIT) was added. The mixture was incubated for 4 hours at 37° C. after which the unmetabolized MTT was removed by aspiration. The formazan crystals were dissolved by adding 200 □L of 95% ethanol. Optical density was measured at 570 nm using a microplate reader. The percentage of NK cell-specific lysis was calculated as follows:

Specific Cytotoxicity (%)=100×{1−[(*OD* of target cells and effector cells−*OD* of effector cells)/(*OD* of target cells)]}

3. Antibody response to vaccines: The test subjects are given an array (up to 5) of vaccines after at least 12 weeks of probiotic or control feeding. The vaccines may be a mixture of novel and redundant vaccines. Non-limiting examples of vaccine arrays that may be used include mixtures of vaccines prepared by Fort Dodge Animal Health. Non-limiting examples of vaccines suitable for use herein include Canine distemper, adenovirus, coronavirus, parainfluenza, and parvovirus. The test subject's vaccine history will determine the vaccines to be used. The specific antibodies to the vaccines given are measured in blood for 3 weeks and the length and strength of response in control and probiotic feeding groups compared.

4. Delayed-type hypersensitivity: An in vivo, non-invasive method of assessing immune system status. This test comprises an intradermal injection of the polyclonal mitogen Phytohemmaglutinin (PHA) in combination with sheep red blood cells a multivalent vaccine, histamine (100 µL of 0.0275 g/L Histamine Phosphate; Greer, Lenoir, N.C.), or PBS (100 µL of Phosphate Buffered Saline, 8.5 g/L; Sigma). The immune response to the antigen is recorded as skinfold thickness using calipers at time intervals of 0, 24, 48 and 72 hours post-injection. An increase in skinfold thickness is indicative of a greater hypersensitivity response that should be decreased by treatment with the bacteria of the present invention.

Additional methods for determining the effect of the *Bifidobacteria* bacteria of the present invention are described in U.S. Pat. Nos. 6,133,323 and 6,310,090.

Furthermore, ameliorating the effects of age may be determined using dual x-ray absorptometry or CT scan for measuring body composition, including body fat mass, fat-free mass and bone mineral content. Similarly, this method may be used to determine anatomy changes such as weight loss or bone density in subjects following infection.

The *Bifidobacteria* of the present invention may also be used in a method for reducing stress levels in companion animals. Concentrations of blood stress hormones including epinephrine, norepinephrine, dopamine, cortisol and C-reactive protein may be measured to determine stress levels and their reduction or maintenance. These hormones are recognized biomarkers of stress and can be readily measured using techniques known to those skilled in the art.

Further still, maintenance or improvement of the health of the skin and/or coat system of companion animals, including atopic disease of the skin, may be measured using skin and coat assessments conducted by two trained individuals. Examples of criteria examined during such assessments include:

a) Shedding index: A shedding index is assigned to each test subject by collecting hair produced during a standardized brushing session. The hair is retained and weighed, and control and test subjects compared.

b) Subjective skin/coat evaluations: Trained panelists subjectively evaluate skin and coat condition by assessing shedding, dander, shine, uniformity, softness and density.

c) Skin functional assessment: The barrier function of the skin may be assessed by wiping the skin surface with an acetone-soaked gauze. This technique effectively disrupts the skin barrier by removing single cell layers and associated lipid fractions of the stratum corneum. Barrier disruption is quantified by measuring the increase in transepidermal water loss (TEWL) and the degree of redness of the insulted site using methods known to those skilled in the art. Redness (erythema) scores are obtained using the previously described camera and lighting system. TEWL readings and redness scores are obtained immediately before and after disruption, and at five and 24-hour endpoints to assess the protective and healing properties of skin.

The treatment or prevention of gastrointestinal infection, including diarrhoea, in companion animals may be measured using stool scores. Stools scores may be recorded daily according to the following guidelines and control and test groups compared before and after feeding with the bacteria according to the present invention.

Score: 5 Extremely Dry
This stool is hard and does not stick to surfaces. Stool will roll when pushed. No indentations are made when stool is picked up. Stool is often defecated in groups of individual stools instead of one complete unit. The stool maintains original shape after collection.

Score: 4 Firm (Ideal Stool)
This stool is firm, well shaped, and cylindrical. This stool does not break apart easily when picked up. This stool may leave residue on surfaces and gloves. This stool is often defecated as one unit. The stool maintains original shape after collection.

Score: 3 Soft, with Shape
This stool is soft, however there are definite shapes. This stool will break apart easily and will definitely leave residue on surfaces and gloves. The stool often loses original shape after collection. This stool is often present with another score but can comprise whole stool sample.

Score: 2 Soft, without Shape
This stool is soft and will have no cylindrical shape. The shape often associated with a "2" is a "cow patty" shape. This stool will lose the original shape when collected and will definitely leave residue on surfaces and gloves. This stool score is often present with another score but can comprise the whole stool sample. This stool sample may spread over an area of several inches.

Score: 1 Liquid
This stool score will always resemble liquid and there may or may not be particulate matter present. This stool will often be defecated in groups of piles instead of one complete unit. Mucous is often present with this stool sample. This stool sample is very difficult to collect and residue is always left on surfaces and gloves. This stool sample may spread over an area of several inches.

In addition, other observations are also recorded, including: blood in stool; foreign object in stool; or mucous in stool.

Furthermore, the treatment of gastrointestinal infection in companion animals may comprise improving microbial ecology of companion animals. Improving the microbial ecology of companion animals preferably comprises reducing the levels of pathogenic bacteria in the faeces of companion animals. The levels of pathogenic bacteria present in the faeces of companion animals may be enumerated using the standard plate count method known to those skilled in the art. More preferably, the pathogenic bacteria are selected from the group consisting of *Clostridia, Escherichia, Salmonella*, bacteriodes and mixtures thereof. Non-limiting examples of suitable strains of pathogenic bacteria include *C. perfringens, C. difficile, Eschericia coli, Salmonella typhimurium* and mixtures thereof.

The method of use of the bacteria of the present invention may also include the treatment, either prophylactic or therapeutic of the urinary tract of mammals, preferably companion animals. Non-limiting examples of urinary tract treatment include treatment or prevention of urinary tract infections, treatment or prevention of kidney disease, including kidney stones, treatment or prevention of bladder infections and the like. Without being bound by theory, it is believed that the *Bifiodbacteria* bacteria of the present invention are useful in preventing these ailments as a result of their ability to degrade oxalic acid, as demonstrated in vitro. Oxalic acid is a by-product of urinary metabolism that can form insoluble precipitates that result in kidney, bladder and other urinary tract infections. By degrading oxalic acid, and therefore potentially preventing its precipitation and build up in the urinary tract, the bacteria of the present invention may treat and prevent infections and other ailments of the urinary tract. Oxalic acid degradation may be measured in vitro using the Oxalic acid test kit cat #755699 commercially available from Boehringer Mannheim/R-Biopharm.

The *Bifidobacteria pseudolongum* of the present invention may be used in a method for improving or maintaining the health of companion animals comprising improving fiber digestion. Improving fiber digestion is desirable as it promotes the growth of said probiotic bacteria, as well as beneficial endogenous microflora, which aid in the suppression of some potentially pathogenic bacteria. In addition, a decrease in the amount of toxic metabolites and detrimental enzymes that result from colonic fermentation has been documented in humans (Tomomatsu, H. "Health effects of oligosaccharides", (1994) *Food Technol*, 48, 61-65). Fiber digestion may be determined using the method described in Vickers et al. (2001), "Comparison of fermentation of selected fructooligosaccharides and othe rfiber substrates by canine colonic microflora", *Am. J. Vet. Res*. 61 (4), 609-615, with the exception that instead of inoculating using diluted fecal samples each experiment used pure cultures of the bacterial strains of interest.

Preferably, the methods of the present invention comprise administration of *Bifidobacteria* selected from the species comprising *Bifidobacteria longum, Bifidobacteria pseudolongum, Bifidobacteria infantis* or *Bifidobacteria globosum*.

Non-limiting examples of probiotic *Bifidobacteria* obtainable by isolation from resected and washed mammlian GI tract useful in the present invention are described in more detail in WO 00/42168 and WO 03/010297.

WO 00/42168 describes probiotic *Bifidobacteria* isolated from resected and washed human GI tract. These bacteria are deposited at the NCIMB under deposit numbers 41050, 41051, 41052, 41053, 41099, and 41100.

WO 03/010297 describes a further example of probiotic *Bifidobacteria* isolated from resected and washed human GI tract. This bacterium is deposited at the NCIMB under the deposit number 41003.

Further examples include strains of *Bifidobacteria globosum* obtainable by isolation from resected and washed canine gastrointestinal tract having probiotic activity in animals. It has been found that strains of *Bifidobacteria* obtainable by isolation directly from resected and washed GI tract of mammals are adherent to the GI tract following feeding of viable bacterial cells, and are also significantly immunomodulatory when fed to animals in viable, non-viable or fractionated form. Without being bound by theory, it is believed that the *Bifidobacteria* obtainable by isolation from resected and washed GI tract closely associate with the gut mucosal tissues. Without further being bound by theory, this is believed to result in the probiotic *Bifidobacteria* generating alternative host responses that result in its probiotic action. It has been found that probiotic bacteria obtainable by isolation from resected and washed GI tract can modulate the host's immune system via direct interaction with the mucosal epithelium, and the host's immune cells. This immunomodulation, in conjunction with the traditional mechanism of action associated with probiotic bacteria, i.e. the prevention of pathogen adherence to the gut by occlusion and competition for nutrients, results in the *Bifidobacteria* being highly efficacious as a probiotic organism.

The *Bifidobacteria* useful in the present invention, obtainable by isolation from resected and washed mammalian GI tract, have in vitro anti-microbial activity against a number of pathogenic bacterial strains/species. Without being bound by theory, it is believed that this in vitro anti-microbial activity is indicative of potential probiotic activity in vivo in animals, preferably companion animals such as canines and felines. The lactic acid bacteria of the present invention preferably have in vitro anti-microbial activity against *Salmonella typhimurium, Listeria monocytogenes, Listeria innocua* or *Eschericia coli*, more preferably a mixture of these strains, more preferably still, all of these strains.

Without being bound by theory, it is believed that the anti-microbial activity of the *Bifidobacteria* bacteria may be the result of a number of different actions by the *Bifidobacteria* bacteria. It has previously been suggested in the art that several strains of bacteria isolated from faecal samples exert their probiotic effect in the GI tract following oral consumption by preventing the attachment of pathogenic organisms to the gut mucosa by occlusion. This requires oral consumption of "live" or viable bacterial cells in order for a colony of bacteria to be established in the gut. However, it is believed that the *Bifidobacteria* useful in the present invention, obtainable by isolation from resected and washed mammalian GI tract, whilst exerting some probiotic effect due to occlusion if given in a viable form, may deliver a substantial probiotic effect in either the viable or non-viable form due to the production during fermentation in vitro of a substance or substances that either inhibit the growth of or kill pathogenic micro-organisms, and/or alter the host animal's immune competence. This form of probiotic activity is desirable, as the bacteria of the present invention can be given as either viable or non-viable cultures or purified fermentation products and still deliver a beneficial therapeutic effect to the host animal.

Preferably, the *Bifidobacteria* bacteria are able to maintain viability following transit through the GI tract. This is desirable in order for live cultures of the bacteria to be taken orally, and for colonisation to occur in the intestines and bowel following transit through the oesophagus and stomach. Colonisation of the intestine and bowel by the lactic acid bacteria of the present invention is desirable for long-term probiotic benefits to be delivered to the host. Oral dosing of non-viable cells or purified isolates thereof induces temporary benefits, but as the bacteria are not viable, they are not able to grow, and continuously deliver a probiotic effect in situ. As a result this may require the host to be dosed regularly in order to maintain the health benefits. In contrast, viable cells that are able to survive gastric transit in the viable form, and subsequently colonise by adhering to and proliferating on the gut mucosa are able to deliver probiotic effects continuously in situ.

Therefore, it is preferable that the lactic acid bacteria of the present invention maintain viability after suspension in a media having a pH of 2.5 for 1 hour. As used herein, "maintain viability" means that at least 25% of the bacteria initially suspended in the test media are viable using the plate count method known to those skilled in the art. Preferably, "maintain viability" means that at least 50% of the bacteria initially suspended are viable. It is desirable for the lactic acid bacteria of the present invention to maintain viability following exposure to low pH as this mimics the exposure to gastric juices in the stomach and upper intestine in vivo following oral consumption in companion animals.

Furthermore, it is preferable that the lactic acid bacteria of the present invention have a growth of at least 33% when in the presence of at least 0.5% porcine bile salts. Growth, as used herein is described in further detail in example 3. More preferably, the bacteria of the present invention have a growth of at least 33% when in the presence of at least 1% porcine bile salts. Without being bound by theory it is believed that the lactic acid bacteria of the present invention, capable of maintaining viability in the presence of at least 0.5% porcine bile salts, are able to survive the conditions present in the intestine. This is thought to be a result of the addition of porcine bile to the culture medium mimicking the conditions of the intestine.

Further still, it is preferable that the *Bifidobacteria* bacteria useful in the present invention have significant adhesion to gut epithelial cells in vitro. As used herein, "significant adhesion" means at least 4% of the total number of lactic acid bacteria co-incubated with the epithelial cells in vitro adhere to the epithelial cells. More preferably, at least 6% of bacterial cells co-incubated adhere to epithelial cells in vitro. Without being bound by theory, it is believed that gut epithelial cell adherence in vitro is indicative of the lactic acid bacteria's ability to colonise the GI tract of an animal in vivo.

The 16s-23s intergenic polynucelotide sequence is known to those skilled in the art as the sequence of DNA in the bacterial genome that can be used in order to identify different species and strains of bacteria. This intergenic polynucelotide sequence can be determined by the method detailed below.

*Bifidobacteria globosum* colonies were picked from an Agar plate and resuspended in IX PCR buffer, heated at 96° C. for 5 minutes, frozen at −70° C. for 5-10 minutes, thawed and an aliquot was added to a PCR eppendorf tube. PCR was performed using the intergenic spacer (IGS) primers, IGS L: 5'-GCTGGATCACCTCCTTTC-3' and IGS R: 5'-CTGGT-GCCAAGGCATCCA-3'. The cycling conditions were 96° C. for 1 min (1 cycle), 94° C. for 30 sec, 53° C. for 30 sec, 72° C. for 30 sec (28 cycles). The PCR reaction contained 5 □l of DNA, PCR buffer (Bioline, UK), 0.2 mM dNTPs (Roche, UK), 0.4 □M IGS L and R primer (150 ng/50 □l) (MWG Biotech, Germany) and Bioline Taq polymerase (0.6 units). The PCR reactions were performed on a Hybaid thermocycler. The PCR products (8 □l) were ran alongside a molecular weight marker (□X174 Hae III, Promega) on a 2% agarose EtBr stained gel in TAE, to determine their IGS profile. Using the same primers as above, the intergenic spacer (IGS) DNA was sequenced for the 2 canine *Bifidobacteria globosum* strains using methods known to those skilled in the art.

Following sequencing, the obtained sequences for the four deposited strains were compared with the on-line sequence database "BLAST", available at http://www.ncbi.nlm.nih.gov/BLAST/ for homology with other deposited bacterial 16s-23s sequences. The closest match for AHCF was *Bifidobacterium pseudolongum* ATCC 25526, having homology scores of 92%. *Bifidobacterium pseudolongum* ATCC25865 was the closest match for AHC 7, having homology scores of 92%. However, the several differences exist between these strains and between each other.

In a preferred embodiment of the present invention, the strain of *Bifidobacteria globosum* has a 16s-23s intergenic polynucleotide sequence that has at least 93%, preferably at least 96%, more preferably at least 99% homology with the polynucleotide sequence according to SEQ. ID NO. 1. More preferably, the strain of lactic acid bacteria according to the present invention has a 16s-23s polynucleotide sequence according to SEQ. ID NO. 1. More preferably still, the strain of lactic acid bacteria according to the present invention is *Bifidobacteria globosum* strain NCIMB 41198 (AHCF), or a mutant thereof.

In another preferred embodiment of the present invention, the strain of *Bifidobacteria pseudolongum*, has a 16s-23s intergenic polynucleotide sequence that has at least 93%, preferably at least 96%, more preferably at least 99% homology with the polynucleotide sequence according to SEQ. ID NO. 2. More preferably, the strain of lactic acid bacteria according to the present invention has a 16s-23s polynucleotide sequence according to SEQ. ID NO. 2. More preferably still, the strain of lactic acid bacteria according to the present invention is *Bifidobacteria pseudolongum* strain NCIMB 41199 (AHC7), or a mutant thereof.

The method of use of the *Bifidobacteria* bacteria of the present invention typically involves oral consumption by the animal. Oral consumption may take place as part of the normal dietary intake, or as a supplement thereto. The oral consumption typically occurs at least once a month, preferably at least once a week, more preferably at least once per day. The *Bifidobacteria* may be given to the companion animal in a therapeutically effective amount to maintain or improve the health of the animal, preferably a companion animal. As used herein, the term "therapeutically effective amount" with reference to the lactic acid bacteria, means that amount of the bacteria sufficient to provide the desired effect or benefit to a host animal in need of treatment, yet low enough to avoid adverse effects such as toxicity, irritation, or allergic response, commensurate with a reasonable benefit/risk ratio when used in the manner of the present invention. The specific "therapeutically effective amount" will vary with such factors as the particular condition being treated, the physical condition of the user, the duration of the treatment, the nature of concurrent therapy (if any), the specific dosage form to be used, the carrier employed, the solubility of the dose form, and the particular dosing regimen.

Preferably, the lactic acid bacteria are given to the companion animal at a dose of from 1.0E+04 to 1.0E+14 CFU per day, more preferably from 1.0E+06 to 1.0E+12 CFU per day. The composition preferably may contain at least 0.001% of from 1.0E+04 to 1.0E+12 CFU/g of the *Bifidobacteria* obtainable by isolation from resected and washed mammalian GI tract. The *Bifidobacteria* bacteria can be given to the animal in either viable form, or as killed cells, or distillates, isolates or other fractions of the fermentation products of the lactic acid bacteria of the present invention, or any mixture thereof.

Preferably, the *Bifidobacteria* bacteria, or a purified or isolated fraction thereof, are used to prepare a composition intended to maintain or improve the health of an animal. As indicated above, the composition may be part of the normal dietary intake, or a supplement. Where the composition comprises part of the normal dietary intake, the composition may be in the form of a dried animal food such as biscuits or kibbles, a processed grain feed, a wet animal food, yogurts, gravies, chews, treats and the like.

Such compositions may comprise further components. Other components are beneficial for inclusion in the compositions used herein, but are optional for purposes of the invention. For example, food compositions are preferably nutritionally balanced. In one embodiment, the food compositions may comprise, on a dry matter basis, from about 20% to about 50% crude protein, preferably from about 22% to about 40% crude protein, by weight of the food composition. The crude protein material may comprise any material having a protein content of at least about 15% by weight, non-limiting examples of which include vegetable proteins such as soybean, cotton seed, and peanut, animal proteins such as casein, albumin, and meat tissue. Non-limiting examples of meat tissue useful herein include fresh meat, and dried or rendered meals such as fish meal, poultry meal, meat meal, bone meal and the like. Other types of suitable crude protein sources include wheat gluten or corn gluten, and proteins extracted from microbial sources such as yeast.

Furthermore, the food compositions may comprise, on a dry matter basis, from about 5% to about 35% fat, preferably from about 10% to about 30% fat, by weight of the food composition. Further still, food compositions comprising the lactic acid bacteria of the present invention may also comprise from about 4% to about 25% total dietary fiber. The compositions may also comprise a multiple starch source as described in WO99/51108.

The compositions of the present invention may further comprise a source of carbohydrate. Grains or cereals such as rice, corn, milo, sorghum, barley, alfalfa, wheat, and the like are illustrative sources. In addition, the compositions may also contain other materials such as dried whey and other dairy by products.

The compositions comprising the bacteria of the present invention may also comprise a prebiotic. "Prebiotic" includes substances or compounds that are fermented by the intestinal flora of the pet and hence promote the growth or development of lactic acid bacteria in the gastro-intestinal tract of the pet at the expense of pathogenic bacteria. The result of this fermentation is a release of fatty acids, in particular short-chain fatty acids in the colon. This has the effect of reducing the pH value in the colon. Non-limiting examples of suitable prebiotics include oligosaccharides, such as inulin and its hydrolysis products commonly known as fructooligosaccharides, galacto-oligosaccarides, xylo-oligosaccarides or oligo derivatives of starch. The prebiotics may be provided in any suitable form. For example, the prebiotic may be provided in the form of plant material which contains the fiber. Suitable plant materials include asparagus, artichokes, onions, wheat or chicory, or residues of these plant materials. Alternatively, the prebiotic fiber may be provided as an inulin extract, for example extracts from chicory are suitable. Suitable inulin extracts may be obtained from Orafti SA of Tirlemont 3300, Belgium under the trade mark "Raftiline". For example, the inulin may be provided in the form of Raftiline (g) ST which is a fine white powder which contains about 90 to about 94% by weight of inulin, up to about 4% by weight of glucose and fructose, and about 4 to 9% by weight of sucrose. Alternatively, the fiber may be in the form of a fructooligosaccharide such as obtained from Orafti SA of Tirlemont 3300, Belgium under the trade mark "Raftilose". For example, the inulin may be provided in the form o Raftilose (g) P95. Otherwise, the fructooligosaccharides may be obtained by hydrolyzing inulin, by enzymatic methods, or by using micro-organisms.

For dried pet foods a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in European patent application No 0850569. If a probiotic micro-organism is used, the organism is best coated onto or filled into the dried pet food. A suitable process is described in European patent publication Number EP 0 862 863.

For wet foods, the processes described in U.S. Pat. Nos. 4,781,939 and 5,132,137 may be used to produce simulated meat products. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers. Typical wet food compositions may comprise from about 5% to about 15% protein, from about 1% to about 10% fat, and from about 1% to about 7% fiber. Non-limiting ingredients that may be used in wet food compositions include chicken, turkey, beef, whitefish, chicken broth, turkey broth, beef broth, chicken liver, brewers rice, corn grits, fish meal, egg, beet pulp, chloride, flax meal, lamb, beef by-products, chicken by-products and mixtures thereof.

In another embodiment, supplement compositions such as biscuits, chews, and other treats may comprise, on a dry matter basis, from about 20% to about 60% protein, or from about 22% to about 40% protein, by weight of the supplement composition. As another example, the supplement compositions may comprise, on a dry matter basis, from about 5% to about 35% fat, or from about 10% to about 30% fat, by weight of the supplement composition. Food and supplement compositions intended for use by canines or felines are commonly known in the art.

The pet foods may contain other active agents such as long chain fatty acids and zinc. Suitable long chain fatty acids include alpha-linoleic acid, gamma linolenic acid, linoleic acid, eicosapentanoic acid, and docosahexanoic acid. Fish oils are a suitable source of eicosapentanoic acids and docosahexanoic acid.

Borage oil, blackcurrent seed oil and evening primrose oil are suitable sources of gamma linolenic acid. Safflower oils, sunflower oils, corn oils and soy bean oils are suitable sources of linoleic acid. These oils may also be used in the coating substrates referred to above. Zinc may be provided in various suitable forms, for example as zinc sulfate or zinc oxide. Further, many ingredients commonly used in pet foods are sources of fatty acids and zinc. It has been observed that the combination of chicory, as a source of prebiotic, with a linoleic-acid rich oil, such as soy bean oil, provides unexpected benefits, suggestive of a synergistic effect.

Where the composition is in the form of a gravy, the composition preferably comprises at least 10% of a broth, or stock, non-limiting examples of which include vegetable beef, chicken or ham stock. Typical gravy compositions may comprise from about 0.5% to about 5% crude protein, from about 2% to about 5% crude fat, and from about 1% to about 5% fiber.

Further non-limiting examples of supplements suitable for use herein include powders, oil suspensions, milk-based suspensions cheeses, and pills or capsules. Where the composition is in the form of a pill, suitable binding agents are required to maintain the pill in a solid, pressed form. Non-limiting examples of suitable binding agents include the natural gums such as xanthan gum, pectins, lecithins, alginates and others known to those skilled in the art. Where the composition is in the form of a capsule, the composition is preferably encapsulated using technologies known to those skilled in the art. Non-limiting, examples of suitable encapsulation materials include polyvinyl alcohol (PVA), polyvinylpyrrolidone (PVP), alginates, and gelatin. Yogurtbased compositions may comprise from about 1% to about 5% protein, from about 10% to about 20% carbohydrate, from about 1% to about 5% fiber, from about 1% to about 5% fat and from about 50% to about 90% liquid carrier such as milk.

EXAMPLES

Examples 1 to 4 are examples of dried kibble compositions comprising the probiotic *Bifidobacteria globosum* utilized in accordance with the present invention.

| Ingredient | Percentage on a weight Basis | | | |
|---|---|---|---|---|
| | Ex. 1 | Ex. 2 | Ex. 3 | Ex. 4 |
| Cereal grains | To 100 | To 100 | To 100 | To 100 |
| Poultry by-product meal | 43.5 | 40 | 45 | 35 |
| Poultry fat | 1.28 | 1.02 | 1.16 | 1.35 |
| Egg product | 2.4 | 2.1 | 2.5 | 2.2 |
| Chicken liver meal | 1.0 | 1.0 | 1.0 | 1.0 |
| Brewer's dried yeast | 1.0 | 1.0 | 1.0 | 1.0 |
| Monosodium phosphate | 1.0 | 1.0 | 1.0 | 1.0 |
| Calcium carbonate | 0.8 | 0.8 | 0.8 | 0.8 |
| Potassium chloride | 0.6 | 0.6 | 0.6 | 0.6 |
| Vitamins | 0.4 | 0.4 | 0.4 | 0.4 |
| Choline chloride | 0.3 | 0.3 | 0.3 | 0.3 |
| Minerals | 0.3 | 0.3 | 0.3 | 0.3 |
| DL-Methionine | 0.1 | 0.1 | 0.1 | 0.1 |
| Sodium Chloride | 0.03 | 0.03 | 0.03 | 0.03 |
| Probiotic ($1 \times 10^{10}$ cfu/g) NCIMB 41198 in sunflower oil) | 1 | 0.5 | — | 0.6 |
| Probiotic ($1 \times 10^{10}$ cfu/g) NCIMB 41199 in sunflower oil) | — | 0.5 | 1 | 0.4 |

Examples 5 to 7 are examples of wet pet food compositions comprising the probiotic *Bifidobacteria globosum* utilized in accordance with the present invention.

| Ingredient | Percentage on a weight Basis | | |
|---|---|---|---|
| | Ex. 5 | Ex. 6 | Ex. 7 |
| Water | To 38 | To 47 | To 50 |
| Poultry Liver | To 25 | To 20 | To 15 |
| Poultry Products | 25 | 20 | 20 |
| Brewers Rice | 5 | 7 | 10 |
| Egg Product | 3 | 2.5 | 1.5 |
| Poultry Fat | 2.9 | 3.0 | 3.2 |
| Chicken Stock | 0.6 | 0.7 | 0.9 |
| Taurine | 0.1 | 0.1 | 0.1 |
| Vitamins | 0.05 | 0.1 | 0.1 |
| Minerals | 0.05 | 0.1 | 0.1 |
| Probiotic NCIMB41003 (1E10 CFU/g) | 4 | 5 | 6 |

Examples 8 to 10 are examples of yogurt supplement compositions comprising the probiotic *Bifidobacteria globosum* utilized in accordance with the present invention.

| Ingredient | Percentage on a weight Basis | | |
|---|---|---|---|
| | Ex. 8 | Ex. 9 | Ex. 10 |
| Milk | 82.75 | 81.9 | 82.7 |
| Sugar | 12 | 12 | 10 |
| Modified Starch | 1.0 | 0.8 | 0.8 |
| Prebiotic | 0.25 | 0.3 | 0.5 |
| Probiotic NCIMB 41052 (1E10 CFU/g) | 4 | 5 | 6 |

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of regulating the immune system of a companion animal comprising administering to the companion animal a probiotic strain of *Bifidobacteria* obtainable by isolation from resected and washed mammalian gastrointestinal tract, wherein said probiotic strain of *Bifidobacteria* is selected from NCIMB 41050, NCIMB 41051, NCIMB 41052, NCIMB 41053, NCIMB 41099, NCIMB 41100, NCIMB 41198, and a mixture thereof.

2. The method according to claim 1, wherein said probiotic *Bifidobacteria* has the ability to survive and colonize the gastrointestinal tract of a companion animal.

3. The method according to claim 1, wherein said probiotic *Bifidobacteria* has at least 33% growth when cultured in the presence of 0.5% bile salts.

4. The method according to claim 2, wherein said probiotic Bifidobacteria is able to maintain viability following 1 hour at pH 2.5.

5. The method according to claim 1, wherein regulating the immune system of a companion animal includes a method selected from the group consisting of treating or preventing autoimmune disease in a companion animal, treating or preventing inflammation in a companion animal, maintaining or improving health of the skin and/ or coat system of a companion animal, treating or preventing atopic disease of the skin in companion animals, ameliorating or reducing the effects of aging in companion animals, preventing weight loss during and following infection in a companion animal, treating or preventing urinary tract ailments in companion animals, increasing fiber digestion in a companion animal, preventing or treating infection of the gastrointestinal tract of a companion animal, reducing stress levels, and combinations thereof.

6. The method according to claim 5, wherein said prevention or treatment of infection of the gastrointestinal tract comprises improving the microbial ecology of said companion animal.

7. The method according to claim 5, wherein said prevention or treatment of infection of the gastrointestinal tract comprises reducing the number of pathogenic bacteria found in the feces of said companion animal.

8. The method according to claim 7, wherein said pathogenic bacteria are selected from the group consisting of *Clostridia, Escherichia, Salmonella*, and a mixture thereof.

9. The method according to claim 5, wherein said stress levels are measured by determining the level in the blood of said companion animal of stress hormones selected from the group consisting of epinephrine, norepinephrine, dopamine, cortisol, C-reactive protein and mixtures thereof.

10. The method according to claim 1, wherein said probiotic *Bifidobacteria* increase the degradation of oxalic acid in vitro.

11. The method according to claim 1, wherein the companion animal is selected from a domestic canine, a feline, a rabbit, a ferret, a horse, and a cow.

12. A method of improving digestion in a companion animal, comprising administering to the companion animal a probiotic strain of *Bifidobacteria* obtainable by isolation from resected and washed mammalian gastrointestinal tract, wherein said probiotic strain of *Bifidobacteria* is selected from NCIMB 41050, NCIMB 41051, NCIMB 41052, NCIMB 41053, NCIMB 41099, NCIMB 41100, NCIMB 41198, and a mixture thereof.

13. The method according to claim 12, wherein said companion animal is selected from the group consisting of a canine and a feline.

14. The method according to claim 12, wherein said probiotic *Bifidobacteria* has the ability to survive and colonize the gastrointestinal tract of a companion animal.

15. The method according to claim 14, wherein said probiotic *Bifidobacteria* is able to maintain viability following 1 hour at pH 2.5.

16. The method according to claim 12, wherein said probiotic *Bifidobacteria* has at least 33% growth when cultured in the presence of 0.5% bile salts.

17. The method according to claim 12, wherein fiber digestion is increased in said companion animal.

18. The method according to claim 12, wherein the companion animal is selected from a domestic canine, a feline, a rabbit, a ferret, a horse, and a cow.

* * * * *